Figure 1:
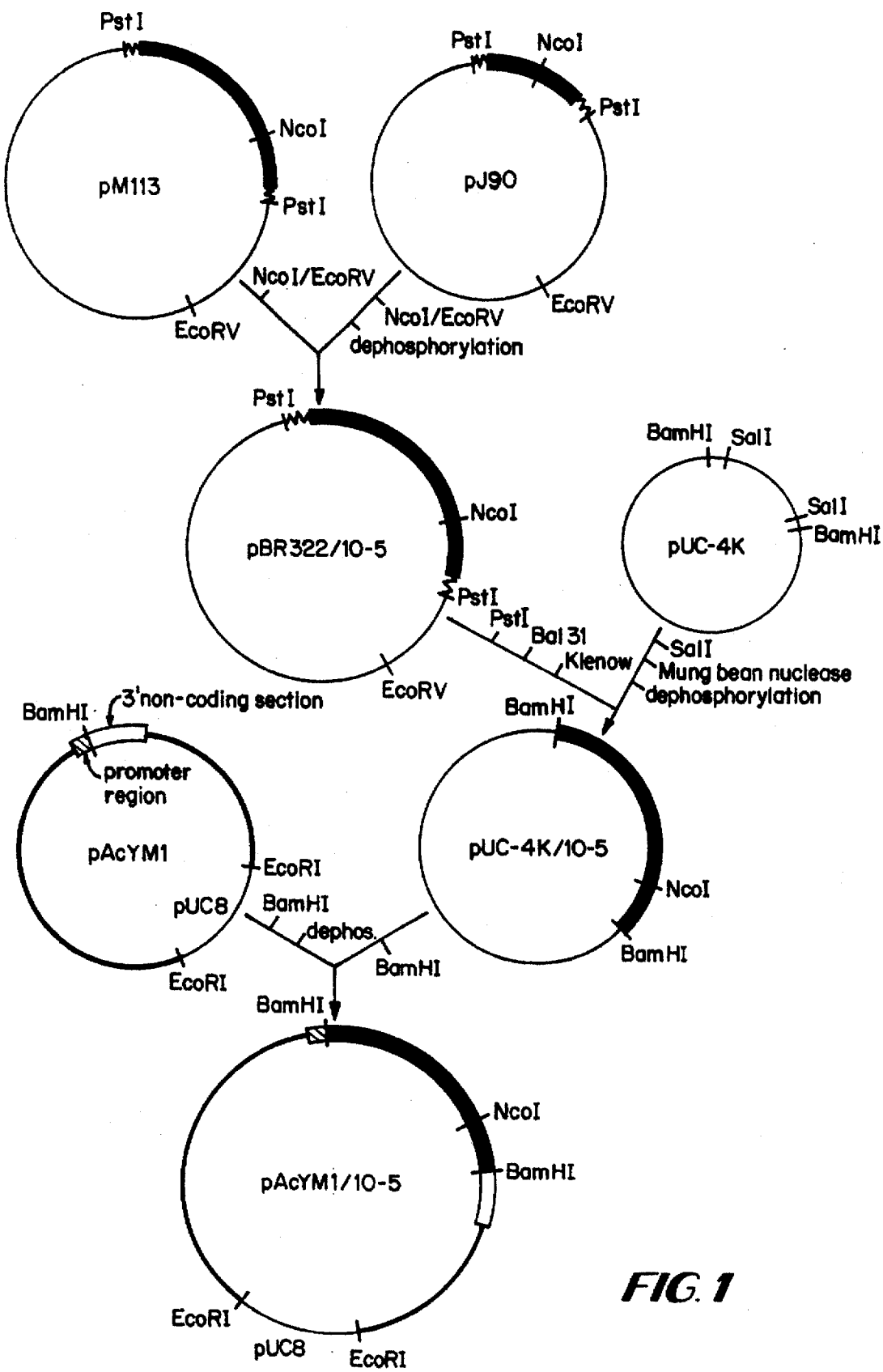

United States Patent [19]

Ermak et al.

[11] Patent Number: 5,690,938
[45] Date of Patent: Nov. 25, 1997

[54] ORAL IMMUNIZATION WITH MULTIPLE PARTICULATE ANTIGEN DELIVERY SYSTEM

[75] Inventors: Thomas H. Ermak; Jacques Pappo; Farshad Guirakhoo; Richard D. Nichols, Jr.; Thomas P. Monath, all of Cambridge, Mass.; Polly Roy, Oxford, England

[73] Assignees: Oravax, Inc., Cambridge, Mass.; Natural Environment Research Council, Swindon, England

[21] Appl. No.: 131,630

[22] Filed: Oct. 5, 1993

Related U.S. Application Data

[63] Continuation-in-part of Ser. No. 853,696, filed as PCT/GB90/01047 Jul. 6, 1990, abandoned.

[30] Foreign Application Priority Data

Jul. 7, 1989 [GB] United Kingdom ............... 8915572

[51] Int. Cl.$^6$ .................................................. A61K 39/15
[52] U.S. Cl. ................... 424/215.1; 435/69.3; 435/172.3
[58] Field of Search ........................... 424/185.1, 186.1, 424/204.1, 215.1; 435/69.3, 172.3; 514/2; 530/350, 826; 536/23.1, 23.72

[56] References Cited

PUBLICATIONS

Holmgren, FEMS Microbiology Immunology vol. 89, pp. 1–10, "Mucosal immunity and vaccination", 1991.

French, T.J et al. J. Virol. 64(4): 1530–36, 1990.

Lycke, N. et al. Immunology 59:301–308, 1986.

Boslego, J.W. et al. "Gonorrhea Vaccines" In: Vaccines and Immunotherapy S.J. Gruz Ed., Pergamon Press, 1991.

Ellis, R.W. "New Technologies for Making Vaccines", In: Vaccines, Plotkin & Mortimer Eds., W.B. Saunders Co. 1988.

French, T.J. et al. J. Virol. 64(12):5695–5700, 1990.

Huismans, H et al. Virology 157: 180–188, 1987.

*Primary Examiner*—Christine M. Nucker
*Attorney, Agent, or Firm*—Nixon & Vanderhye

[57] ABSTRACT

Method of inducing a mucosal and or/systemic immune response in a host, comprising the step of administering to the host an effective amount of a Bluetongue antigen in the form of virus like and/or virus core like particles. Vaccines are also provided.

5 Claims, 16 Drawing Sheets

FIG. 2 pAcYM1    —GTAATAAAAAAACCTATAAATACGGATCCGGTTATT—
                                    <u>BamHI</u> pAcYM1/10-5    —GTAATAAAAAAACCTATAAATACGGATCCGGTTAAAAAGTGTTCTCCTACTCGCAGAAG[ATG]GGGAA—
                                    <u>BamHI</u>                      → BTV-10 segment 5 pAcYM1/10-5    —ACGAAATGCT[TGA]ACGCGGATCCGGTTATT—
                              BTV-10 segment 5 ↓        <u>BamHI</u> pAcYM1/10-2    —GTAATAAAAAAACCTATAAATACGGATCCGGGGTTAAAGAGTGTTCTACC[ATG]GAGAA—
                                    <u>BamHI</u>         |tail|  → BTV-10 segment 2

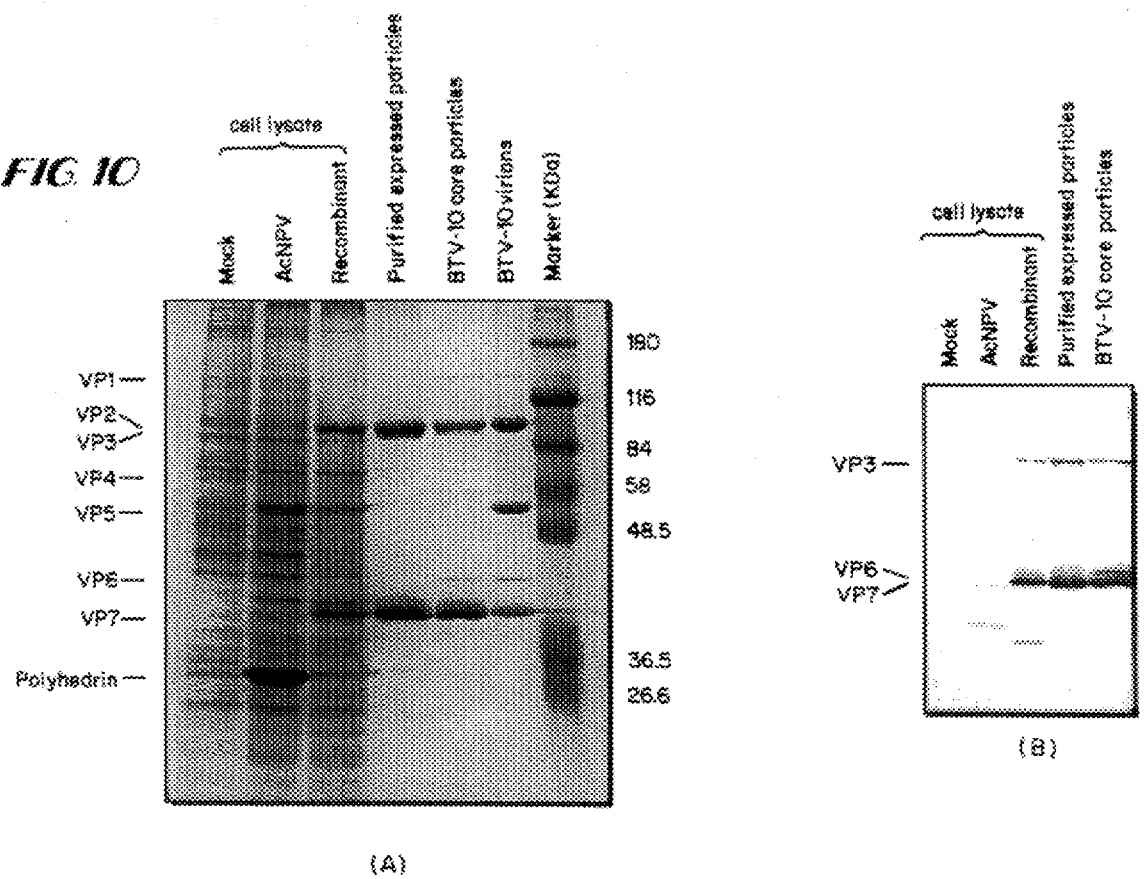

| | | MUCOSAL IgA ANTIBODY (ng/ml) | | | | | |
|---|---|---|---|---|---|---|---|
| | | DAY 17 | DAY 27 | DAY 37 | MEAN DAY 17 | MEAN DAY 27 | MEAN DAY 37 |
| PBS 0 | | 0 | 0 | 0 | | | |
| PBS L | | 0 | 0 | 0 | | | |
| PBS LL | | 0 | 0 | 0 | 0+0 | 0+0 | 0+0 |
| PBS R | | 0 | 0 | 0 | | | |
| PBS RR | | 0 | 0 | 0 | | | |
| VLP+CT 0 | | 0 | 30 | 355 | | | |
| VLP+CT L | | 0 | 0 | 106 | | | |
| VLP+CT LL | | 0 | 0 | 0 | 0.4+0.4 | 28+22 | 621+507 |
| VLP+CT R | | 0 | 0 | 12 | | | |
| VLP+CT RR | | 2 | 112 | 2633 | | | |
| CLP+CT 0 | | 49 | 567 | --- | | | |
| CLP+CT L | | 51 | 393 | 1432 | | | |
| CLP+CT LL | | 29 | 811 | 1498 | 47+5 | 844+224 | 1411+64 |
| CLP+CT R | | 58 | 1691 | 1197 | | | |
| CLP+CT RR | | 49 | 756 | 1515 | | | |
| CLP 0 | | 0 | 6 | 23 | | | |
| CLP L | | 0 | 12 | 0 | | | |
| CLP LL | | 5 | 5 | 0 | 5+5 | 9+4 | 7+5 |
| CLP R | | 0 | 0 | 0 | | | |
| CLP RR | | 0 | 21 | 13 | | | |

| | SERUM IgG ANTIBODY (ng/ml) | | | | | | |
|---|---|---|---|---|---|---|---|
| | DAY 17 | DAY 27 | DAY 37 | | MEAN DAY 17 | MEAN DAY 27 | MEAN DAY 37 |
| PBS 0 | 0 | 0 | 0 | | | | |
| PBS L | 0 | 0 | 0 | | | | |
| PBS LL | 0 | 0 | 0 | | 0+0 | 0+0 | 0+0 |
| PBS R | 0 | 0 | 0 | | | | |
| PBS RR | 0 | 0 | 0 | | | | |
| VLP+CT 0 | 191 | 20911 | 36684 | | | | |
| VLP+CT L | 0 | 4182 | 7302 | | | | |
| VLP+CT LL | 237 | 3864 | 10805 | | 132+55 | 9219+3457 | 21361+5474 |
| VLP+CT R | 0 | 3699 | 23527 | | | | |
| VLP+CT RR | 232 | 13439 | 28485 | | | | |
| CLP+CT 0 | 628 | 32378 | --- | | | | |
| CLP+CT L | 471 | 9183 | 22822 | | | | |
| CLP+CT LL | 977 | 23242 | 79012 | | 500+145 | 16044+5024 | 32673+13487 |
| CLP+CT R | 131 | 7438 | 14823 | | | | |
| CLP+CT RR | 295 | 7981 | 14033 | | | | |
| CLP 0 | 537 | 3641 | 6741 | | | | |
| CLP L | 0 | 3440 | 2907 | | | | |
| CLP LL | 872 | 8029 | 8271 | | 334+167 | 3401+1313 | 5786+1910 |
| CLP R | 0 | 249 | 146 | | | | |
| CLP RR | 261 | 1644 | 10866 | | | | |

| | | SERUM IgA ANTIBODY (ng/ml) | | | | | |
|---|---|---|---|---|---|---|---|
| | DAY 17 | DAY 27 | DAY 37 | | MEAN DAY 17 | MEAN DAY 27 | MEAN DAY 37 |
| PBS 0 | 0 | 0 | 0 | | | | |
| PBS L | 0 | 0 | 0 | | | | |
| PBS LL | 0 | 0 | 0 | | 0+0 | 0+0 | 0+0 |
| PBS R | 0 | 0 | 0 | | | | |
| PBS RR | 0 | 0 | 0 | | | | |
| VLP+CT 0 | 0 | 83 | 1992 | | | | |
| VLP+CT L | 0 | 0 | 0 | | | | |
| VLP+CT LL | 0 | 0 | 0 | | 0+0 | 143+123 | 2108+808 |
| VLP+CT R | 0 | 0 | 0 | | | | |
| VLP+CT RR | 0 | 630 | 4047 | | | | |
| CLP+CT 0 | 108 | 1280 | --- | | | | |
| CLP+CT L | 37 | 1921 | 4514 | | | | |
| CLP+CT LL | 0 | 831 | 1921 | | 37+19 | 1808+389 | 4128+924 |
| CLP+CT R | 17 | 3138 | 6907 | | | | |
| CLP+CT RR | 23 | 1869 | 3170 | | | | |
| CLP 0 | 0 | 0 | 0 | | | | |
| CLP L | 0 | 0 | 0 | | | | |
| CLP LL | 29 | 0 | 0 | | 5.8+5.8 | 0+0 | 0+0 |
| CLP R | 0 | 0 | 0 | | | | |
| CLP RR | 0 | 0 | 0 | | | | |

ORAL IMMUNIZATION WITH MULTIPLE PARTICULATE ANTIGEN DELIVERY SYSTEM

This application is a continuation-in-part of application Ser. No. 07/853,696, filed Jun. 3, 1992, abandoned which is a 371 of PCT/GB90/01047, filed Jul. 6, 1990.

This invention relates to the delivery of antigens in particulate form to a host. More particularly, the invention relates to the use of virus-like particles (VLP's) or virus core-like particles (CLP's) as an oral antigen delivery system for inducing both mucosal IgA and/or systemic IgG immune responses in a host.

BACKGROUND OF THE INVENTION

Bluetongue virus (BTV) is the prototype virus of the Orbivirus genus (Reoviridae family). It is vectored to vertebrates by Culicoides species and causes disease in certain ruminants, notably sheep.

The genome consists of ten double-stranded RNA segments, each of which is monocistronic, and is located in the core of the virion. The icosahedral core contains two major (VP3 and VP7) and three minor protein species (VP1, VP4, VP6) and is surrounded by a diffuse coat of the proteins VP2 and VP5 (Verwoerd et al. 1972) which are coded for the RNA segments L2 and M5 respectively (Mertens et al., 1984). It is known that VP2 is the main serotype specific antigen (Huismans and Erasmus, 1981; Kahlon et al, 1983).

The genome of BTV consists of 10 unique double-stranded (ds) RNA molecules, each believed to code for a single polypeptide product (Gorman et al, 1981); Sanger and Mertens, 1983). The ten dsRNA species are contained in an inner core structure that contains five types of proteins. The CLP's consist of two essential proteins (VP3 and VP7), with a diameter of about 65 nm and may also include minor components (VP1, VP4 and VP6). The core is surrounded by an outer capsid consisting of two major proteins, VP2 and VP5, to give a complete virus-like particle, the VLP1 with a diameter of approximately 85 nm.

Uptake of antigens and delivery to immunocompetent cells in gut-associated intestinal lymphoid tissues (GALT) are critical factors in the generation of mucosal immune responses (1–3). Interaction between GALT and ingested antigens results in the activation of IgA antibody producing cells and immunoregulatory T cell subsets (4–8). M cells in the follicle epithelium GALT are specialized epithelial cells which transport macromolecules and particulates from the intestinal lumen (3,9).

M cells take up and transport protein antigens (3,10,11), viruses (12), bacteria (13), and protozoa (14) to lymphoid cells within and below the epithelium. The M cell surface has been shown to be a specialized site for binding of *E. coli* strain RDEC-1(15), and for binding and uptake reovirus (18) and *Vibrio cholera* (19). M. cells transport a range of particle sizes including macromolecules such as ferritin (10 nm diameter) (11) to liposomes (20–200 nm) (16) and latex of biodegradable microspheres (0.5–10 μm) (17–20). By targeting M cell surfaces, intestinal uptake of particulates can be augmented (20).

VLP's are 60–90 nm particles with multiple copies of capsid surface proteins (21–26) and may be antigenic when administered systematically (27–29). Foreign epitopes can be inserted into CLP and VLP proteins primarily on VP7 on the surface of CLPs (30).

SUMMARY OF THE INVENTION

It has now been found, surprisingly, according to the present invention that Bluetongue VLP's and CLP's, when administered orally, induce both mucosal and systemic immunity in the host. In addition, it has been found that Bluetongue VLP's and CLP's can function as carriers for foreign epitopes, and can induce immunity against the foreign epitope when administered. These particles are composed of proteins arranged in layers with certain proteins interacting to form an outer coat or capsid, and others forming the core or inner capsid. Virus proteins that are capable of assembling in the absence of viral nucleic acids form VLP's, whereas proteins which normally form the core are termed CLP's.

In first aspect, the present invention provides a method of inducing a mucosal and or/systemic immune response in a host, comprising the step of administering to said host an effective amount of a Bluetongue antigen in particulate form. Preferably, the particulate antigen is administered orally. and may be in the form of virus like particles or virus core like particles. The virus like particles preferably comprise at least one of VP3, VP7, VP2 and VP5, and the virus core like particles preferably comprise at least one of VP3 and VP7.

From the above, it will be understood that it is possible to genetically engineer proteins of completely unrelated viruses and bacteria into VLP's and CLP's. The resulting chimeric VLP's and CLP's may be used as vaccines to induce immunity against the selected agent incorporated. VLP's and CLP's composed solely of Bluetongue proteins may be used to protect animals, notably sheep, against Bluetongue virus disease, VLP's and CLP's may also be produced from viruses related to Bluetongue, especially African Horsesickness. Moreover, it is possible to incorporate foreign proteins to produce vaccines, especially oral vaccines, against diseases such as hepatitis B, Clostridium difficile, Helicobacter pylori, influenza, parainfluenza, respiratory syncytial virus (RSV), rotavirus and HIV.

It has also been found, according to the invention, that recombinant expression vectors can be effectively used to achieve expression of BTV structural protein VP2 and/or VP5 in antigenic form capable of raising neutralizing antibodies and consequently being suitable for use as vaccine components.

Further, BTV structural proteins have hitherto been expressed in insect cells, but it has not been demonstrated previously that any BTV structural proteins produced by recombinant DNA technology are capable of raising neutralizing antibodies and consequently are suitable for use as a delivery system and as vaccine components. We have now demonstrated that BTV proteins expressed in this way are suitable for both of these purposes.

According to another aspect of the present invention, a polypeptide comprising at least an antigenic portion of at least one of bluetongue virus structural proteins VP2 and VP5 in antigenic form is used as a vaccine component, wherein the polypeptide is produced by transforming a host with a recombinant expression vector having a DNA segment coding for the polypeptide.

According to a preferred aspect of the invention, the polypeptides are produced by infecting susceptible insects or cultured insect cells with one or more expression vectors having a DNA segment coding for the polypeptides.

The invention further provides a method of obtaining a protective effect against bluetongue infection in mammals (particularly ruminants) which comprises inoculating the mammals with a polypeptide comprising at least an antigenic portion of bluetongue virus structural protein VP2 in antigenic form, wherein the polypeptide is produced by transforming a host with a recombinant expression vector having a DNA segment coding for the polypeptide.

The polypeptide is preferably produced by infecting susceptible insects or cultured insect cells with an expression vector having a DNA segment coding for the polypeptide.

It has further been found that an enhanced protective effect may be achieved by the combined use as a vaccine component, of at least an antigenic portion of bluetongue virus structural protein VP2 (produced as described above) and a polypeptide comprising at least an antigenic portion of bluetongue virus structural protein VP5, the structural protein VP5 also being produced by transforming a host with a recombinant expression vector having a DNA segment coding for the polypeptide. As above, preferably the VP5 polypeptide is produced by infecting susceptible insects or cultured insects cells with an expression vector having a DNA segment coding for the polypeptide.

Thus, preferably, mammals are further inoculated with a second polypeptide comprising at least an antigenic portion of bluetongue virus structural protein VP5 in antigenic form, wherein the second polypeptide is produced by transforming a host with a recombinant expression vector having a DNA segment coding for the polypeptide. The host preferably comprises susceptible insect or cultured insect cells.

Also provided according to the invention is the use of a polypeptide comprising at least an antigenic portion of BTV structural protein VP2 in the manufacture of a vaccine composition for carrying out the above method, wherein the polypeptide is produced as described below.

The use of a polypeptide comprising of at least an antigenic portion of BTV structural protein VP5 in the manufacture of such a vaccine composition, wherein the polypeptide is produced by infecting susceptible insects or cultured insect cells with an expression vector having a DNA segment coding for the polypeptide also forms a part of the present invention.

In another aspect of the invention, there is provided a vaccine compostion suitable for inducing a mucosal and/or systemic response when administered to a host, comprising at least an antigenic protion of Bluetongue virus in particulate form and in an amount effective to induce the desired mucosal and/or systemic response. The compositions preferably also comprise a pharmaceutically acceptable carrier and/or diluent known in the art, as well as a pharmaceutically acceptable adjuvant. A typical example of such an adjuvant is cholera toxin.

According to a further aspect of the invention, there is provided a vaccine composition comprising a polypeptide comprising at least an antigenic portion of bluetongue virus structural protein VP2 in antigenic form, wherein the polypeptide is produced as described above, preferably by infecting susceptible insects or cultured insect cells with an expression vector having a DNA segment coding for the polypeptide.

The vaccine preferably also additionally comprises a polypeptide comprising at least an antigenic portion of bluetongue virus structural protein VP5 in antigenic form, wherein the polypeptide is produced as described above, preferably by infecting susceptible insects or cultured insect cells with an expression vector having a DNA segment coding for the polypeptide.

Surprisingly, it has been found that transformed insects and cultured insect cells are capable of producing bluetongue virus structural proteins VP2 and VP5 in morphological forms which are capable of raising neutralizing antibodies in mammals.

Especially suitable expression vectors for transforming the insects or insect cells are those based on baculoviruses. Thus, for example, the expression vectors used in the method of the invention may comprise a recombinant baculovirus having a DNA segment coding for a polypeptide comprising a bluetongue virus structural protein VP2 and/or VP5.

Such recombinant baculoviruses may include promoter systems native to naturally occurring baculoviruses, for example the so-called "polyhedrin" promoter, or they may include other promoter systems capable of directing expression of polypeptide in transformed insect or cultured insect cells.

Especially suitable cultured insect cells are those of *Spodoptera frugiperda*.

For the simultaneous expression of different bluetongue proteins utilizing a baculovirus-based expression system it is advantageous to use the so-called "multiple expression system" which is the subject of published International Patent Application WO89/01518 (incorporated herein by reference). The procedure described in WO89/01518 utilizes a plasmid designated pAcVC3 which has been deposited at the National Collection of Industrial Bacteria under Accession No. NCIB12516.

pAcVC3 contains duplicated copies of the polyhedrin transcriptional machinery from *Autographa californica* nuclear polyhedrosis virus (AcNPV). This enables a recombinant baculovirus to be constructed which will express two foreign polypeptides simultaneously in *Spodoptera frugiperda* insect cells. In pAcVC3, a unique enzyme restriction site located downstream of each promoter allows for the insertion of two foreign genes, each of which will be placed under the control of its own copy of the polyhedrin transcriptional machinery. The promoters are present in opposite orientations to minimize the possibility of homologous sequence recombination and excision of one or other of the foreign genes.

Bluetongue CLPs have been produced using baculovirus, *Autographa californica* nuclear polyhedrosis virus (AcNPV), containing gene inserts for VP3 (from BTV-17) and VP7 (from BTV-10). The baculovirus was grown in Sf-9 cells (ovarian tissue of the pupa of the Fall army worm, *Spodoptera frugiperda*) at 280° C. in TC100 medium (25, 26,30). AcNPV were produced using large volume spinner flask cultures. Baculovirus titer was determined by conventional plaque assay procedures. Infected AcNPV-BTV17.3-10.7 cells were harvested, centrifuged and homogenized, and CLPs were purified on a discontinuous sucrose gradient (30/66%). Sucrose was removed by dialysis and CLP particles concentrated to $10^8$–$10^{12}$ particles/ml. CLPs were farther purified on CsCl gradient and characterized by 10% SDS-page, electron microscopy, Western blotting, Lowry protein assay and ELISA using anti-VP7.

Bluetongue VLPs were produced in Sf-9 cells containing gene inserts for VP3, VP7, VP2 and VP5 (AcBTV17.3-10.7+AcBTV10-2-5). VLPs were produced as were CLPs and characterized by 10% SDS-page, electron microscopy, and Western blotting.

BTV 10 was grown in BHK-21 cells and Vero cells in MEM. Cells were lysed in Tris buffer and BTV isolated by centrifugation and purified on sucrose gradient. BTV was characterized by SDS-page, Western blot analysis, and electron microscopy and the viral concentration adjusted to $10^8$–$10^{12}$ particles/ml.

The VP2 and/or VP5 polypeptides advantageously are produced for incorporation into vaccines according to the invention by expressing the polypeptides together with other polypeptides having the capacity to self-assemble, whereby the polypeptides are able to form assembled antigen particles, which in many instances resemble the native viruses themselves, both in morphology and antigenic properties.

Examples of proteins having a capacity to self-assemble are bluetongue proteins VP3 and VP7, or VP3, VP7, VP2, and VP5.

The production of antigen particles proteins having a capacity to self-assemble is described and claimed in published International Patent Application No. (corresponding to GB 8915571.7) (incorporated herein by reference). The assembled particles so-produced can include VP2 and VP5 polypeptide.

The expression and characterization of the BTV serotype 10 (BTV-10) VP2 and VP5 gene products using expression systems based on recombinant baculoviruses is illustrated by the following Examples. As indicated, the expressed protein has been shown to be capable of inducing a protective effect when used as a vaccine component, especially when administered in combination with the VP5 gene product.

BRIEF DESCRIPTION OF THE DRAWINGS

The present invention will now be described in more detail with reference to the accompanying drawings in which FIG. 1 is a schematic diagrams of the construction of the transfer vector PacYM1/10-5 as described in Methods;

FIG. 2 is a Sequence around the insertion sites of transfer vectors pAcYM1/10-5 and pAcYM1/10-2. BTV coding sequences are underlined and start and stop codons are boxed (SEQ ID NOS:1–4).

FIG. 3 shows a Southern analysis of vital DNA isolated from YM1/10-5 and AcNPV infected *S. frugiperda* cells and pAcYM1/10-5 transfer vector DNA probed with nick translated segment 5 DNA as described below in Methods.

FIG. 4 shows a SDS-PAGE analysis of mock, AcNPV, YM1/10-5 and YM1/10-2 infected *S. frugiperda* cells. The positions of the VP5, VP2 and polyhedrin protein bands are marked along with the positions of molecular weight markers run at the same time.

FIGS. 5(A), (B) and (C) show immunoblotting of expressed and authentic BTV proteins. Protein extracts of *S. frugiperda* cells infected with YM1/10-5, YM1/10-2 or AcNPV and BHK cells mock and BTV-10 infected were resolved by 10% SDS-PAGE and electrophoretically blotted as described in Methods. In (A), the membrane was probed with rabbit sera raised to BTV-10 virions. In (B) the membrane was probed with mouse ascitic fluid raised to expressed VP5 and in (C) the membrane was probed with rabbit sera raised to expressed VP2. The positions of the VP2 and VP5 proteins are indicated as well as those of molecular weight markers.

FIGS. 6(A) and (B) show pulse-chase (35S) methionine labelling time course of *S. frugiperda* cells either mock, AcNPV (NPV) or YM1/10-5 infected for 24 hours. After labelling the cells were chased for 0, 4, 8, 16 and 24 hours as described in Methods. Protein extracts were then resolved by SDS-PAGE and autoradiography either untreated (A) or after immune precipitation with rabbit anti BTV-10 antisera (B). The positions of VP5 and polyhedrin proteins as well as molecular weight markers and indicated.

FIG. 7 shows constructions of the baculovirus expression transfer vector containing the L2 and M5 genes of BTV serotype 10. The cloning, genetic manipulations, and individual expression of these genes have previously been described. The L2 and M5 genes were excised from their single baculovirus expression transfer vector (pAcYM1) and ligated into the BglII and BamHI sites respectively of the multiple vector pAcVC3.

FIGS. 8(A), (B) and (C) show expression of the four major BTV structural proteins VP2, VP3, VP5 and VP7 in insect cells by recombinant baculoviruses, and confirmation of their authenticity by Western Immunoblot analysis. *S. frugiperda* cells were infected at a multiplicity of 5 pfu/cell with either the recombinant baculovirus expressing VP2 and VP5, or the recombinant expressing VP3 and VP7, or were co-infected with both recombinant viruses. Mock and wild-type AcNPV infected cells acted as controls. Cells were harvested at 48 h post-infection, washed with PBS and lysed at 4° C. in 50 nM Tris-HCl pH8.0, 150 mM NaCl, 0.5% NP40. The expressed particles (both single-shelled core-like particles and double-shelled virus-like particles) were purified by bending at the interface of a 30% w/v, and 66% w/v discontinuous sucrose gradient (in 0.2M Tris-HCl, pH8.0) after centrifugation at 85,000 g for 3 h. Authentic BTV virions prepared from BTV-infected BHK cells are included for comparison. Proteins were separated by SDS-PAGE cells and stained with Coomassie Blue (A), or were electroblotted onto Immobilon membrane and reacted with rabbit BTV-10 antiserum (B). Since VP2 co-migrates with VP3, its presence in the purified double-shelled virus-like particles and authentic BTV virions was confirmed by reacting with antisera raised to expressed VP2 (C). Bound antibody was detected with an alkaline phosphatase conjugate using standard methods.

FIGS. 9A and 9B show construction diagrams of the dual expression transfer vector showing the appropriate manipulations for the insertion of the BTV L3 and M7 genes.

FIGS. 10(A) and (B) show expression of the BTV core proteins VP3 and VP7 in insect cells by the recombinant baculovirus, and confirmation of their authenticity by Western blot analysis. *S. frugiperda* cells were infected at a multiplicity of 10 pfu/cell with recombinant virus, wild-type AcNPV, or were mock infected. Cells were harvested at 48 h post-infection, washed with PBS and lysed at 4° C. in 50 nM Tris-HCl pH 8.0, 150nM NaCl,0.5% NP40. The expressed particles were purified by banding at the interface of a 30% w/v, 50% w/v discontinuous sucrose gradient (in 0.2 M Tris-HCl pH 8.0) after centrifugation at 85,000 rpm for 3 h. Authentic BTV virions and core particles prepared from BTV-infected BHK cells are included for comparison. Proteins were separated by SDS-PAGE and stained with Coomassie blue (A), or were electroblotted onto immobilion membrane, and reacted with rabbit anti BTV-10 serum (B). Bound antibody was detected with an alkaline phosphatase conjugate by the standard method.

FIGS. 11(A), (B) and (C) show electron micrographs of empty BTV core particles synthesized in insect cells by a recombinant baculovirus expressing both major BTV core proteins VP3 and VP7 (A) sections of *S. frugiperda* cells infected with the recombinant (1), or wild-type AcNPV virus (2). (B) purified expressed particles (3) compared with authentic BTV core particles (4).

FIGS. 12(A), (B), (C) and (D) show electron micrographs of baculovirus expressed particles. Empty BTV double-shelled virus-like particles are shown in (A) compared with authentic BTV particles (B). The high magnification micrographs (x30,000) show the appearance of expressed core-like particles composed of VP3 and VP7 (C), and the double-shelled particles with VP2 and VP5 attached to VP3 and VP7 (D).

FIGS. 13–15 show, respectively, the results of oral administration of CLP's and VLP's in terms of the generation of a mucosal IgA response, a serum IgA response and a serum IgG response.

EXAMPLES

Virus and Cells. AcNPV and recombinant baculoviruses were grown and assayed in either confluent monolayers or spinner cultures of *Spodoptera frugiperda* cells in medium containing 10% (v/v) fetal bovine serum according to the procedures described by Brown and Faulkner (1977).

DNA manipulation and construction of DNA clones. Plasmid DNA manipulations were carried out following the procedures described by Maniatis et al (1982). Restriction enzymes, T4 DNA ligase, mung bean nuclease and Bal 31 nuclease were purchased from Amersham International plc (Amersham, UK) and calf intestine alkaline phosphatase from Boehringer Manheim GmbH (FGR). Two BTV-10 segment 5 DNA clones, pM113 and pJ90, representing nucleotides 1–1314 and 992–1638 of the gene respectively (Purdy et al 1986) were used to construct a single copy of the entire gene using a unique NcoI site present in the overlapping regions and the unique EcoRV site of pBR322.

Insertion of BTV-10 segment 5 and segment 2 DNA into pAcYM1. The plasmid pBR322/10-5 was digested with Pst I and the 1.6 Kb fragment containing the complete VP5 gene was recovered and digested with Bal 31 exonuclease to eliminate the terminal dC-dG sequences which were introduced during the cDNA cloning process. The product DNA was repaired with the Klenow fragment of DNA polymerase and ligated into the dephosphorylated vector pUC-4K which had previously been digested with Sal I and the overhanging 5' ends blunted by Mung bean nuclease. The recombinant pUC-4K/10-5 vectors were characterized by appropriate restriction enzyme digests and dideoxy sequence analysis of the double stranded plasmid DNA (Chen and Seeburg, 1985). One of these recombinant vectors had all of the terminal dC-dG sequences removed, this vector was digested with BamHI and the fragment containing the coding sequence of the gene isolated. This fragment was ligated into the baculovirus transfer vector pAcYM1 (Matsuura et al, 1987) which had previously been digested with BamHI and dephosphorylated. The orientation of the recombinant vectors was characterized by restriction mapping and dideoxy sequence analysis of the double stranded plasmid DNA. The baculovirus transfer vector pAcSI10.2 previously described (Inumaru and Roy, 1987) was digested with BamHI and the 2.9 Kb fragment containing the complete BTV-10 VP2 gene isolated. This fragment was ligated into the baculovirus transfer vector pAcYM1 which had previously been digested with BamHI and dephosphorylated. The orientation of the recombinant vectors was characterized by restriction mapping and dideoxy sequence analysis of the double stranded plasmid DNA.

Transfection and selection of recombinant baculoviruses. S. frugiperda cells were transferred with mixtures of infectious AcNPV DNA and pAcYM1/10-5 or pAcYM1/10-2 plasmid DNA. Recombinant baculoviruses were obtained as described previously (Inumaru and Roy, 1987). One recombinant derived from pAcYM1/10-5 was designated YM1/10-5 and one derived from pAcYM1/10-2 was designated YM1/10-2.

Extraction and characterization of viral and cellular nucleic acids. To obtain recombinant viral DNA 100 ml spinner cultures of S. frugiperda cells were infected at a multiplicity of 0.1 p.f.u./cell and incubated at 28° C. for 4 days. The procedures used for virus isolation and subsequent viral DNA extraction were essentially the same as those described previously (Matsuura et al, 1986). For Southern analysis (Southern, 1975) these preparations were digested to completion with BamHI and the products resolved by electrophoresis in 0.8% (w/v) agarose (BRL, Madison, Wis.) and then blotted onto HYBOND-N (Amersham, UK) and dried. The blotted DNA was probed with BTV-10 segment 5 DNA or segment 2 DNA, obtained from the transfer vectors pAcYM1/10-5 or pAcYM1/10-2, that had been 32P labelled by nick translation. The membrane was then washed and autoradiographed.

Production and immunological characterization of proteins. S. frugiperda cells were infected with either recombinant virus (YM1/10-5 or YM1/10-2), wild type AcNPV or mock infected at a multiplicity of 10 p.f.u./cell in 35 mm tissue culture dishes ($1.5 \times 10^6$ cells/dish) and incubated at 28° C. hours. For analysis of protein by immunoblotting or Coomassie blue staining SDS-PAGE gels the cells were harvested and washed in cold phosphate buffered saline (PBS) and then resuspended in 100 μl of RIPA buffer (0.5M Tris-CL, 0.13M NaCl, 1% (v/v) TRITON X-100 (non-ionic detergent), 1% (w/v) sodium deoxycholate, 0.01M EDTA, pH7.4). For analysis of proteins by immunoprecipitation the cells were subsequently incubated at 28° C. for 1 hour in methionine and serum free medium to reduce the intracellular methionine pool. The cells were then labelled with 30 μCi of [35S]methionine (Amersham, 800 Ci/mmol) in methionine and serum free medium for 1 hour at 28° C. and then chased for varying times at 28° C. with medium containing unlabelled methionine. At the end of the chase period the cells were washed twice in cold PBS and resuspended in 100 μl of RIPA buffer: Fifty μl aliquots of these extracts were then incubated with 50 μl of a 1 in 50 dilution of rabbit BTV-10 antisera at 37° C. for 90 minutes. Then 25 μl of a 100 mg/ml suspension of protein A-sepharose CL-4B beads were added and the mixture incubated at 37° C. for a further two hours. At the end of this time the beads were washed twice with ice cold RIPA buffer and once with ice cold PBS and the immune complexes were removed from the beads by boiling for 5 minutes in SDA-PAGE sample buffer (2.3% (w/v)SDA, 10% (v/v)glycerol, 5% (v/v)) mercaptoethanol, 62.5 mM Tris-CL, 0.01% (w/v) bromophenol blue, pH 6.8). Aliquots of the supernatant were subjected to electrophoresis in 5% to 15% gradient gels of acrylamide as described by Laemmli (1970). After electrophoresis the gels were fixed in 40% (v/v) methanol, 10% (v/v) acetic acid and in water, dried and exposed to X-ray film.

Production of antisera in mice and rabbits. Recombinant VP5 and VP2 were run on 10% SDS-PAGE gels and the protein bands visualized by staining in 0.25M KCl and destaining in tap water, both at 4° C. The bands corresponding to the recombinant proteins were excised and macerated by passing the gel through a 23 G syringe needle before use for immunization. In the case of rabbits each animal received one intramuscular injection of antigen in Freunds complete adjuvant followed by three injections of antigen in Freunds incomplete adjuvant on days 11, 20 and 52. The animal was terminally bled by cardiac puncture 29 days after the last injection. For mice each animal received one injection of antigen in Freunds complete adjuvant intraperitoneally followed by two injections of antigen in Freunds incomplete adjuvant on day 7 and day 19, then $5 \times 10^6$ Ehrlich's ascites cells on day 25 and a final injection of antigen in Freunds incomplete adjuvant on day 26. Ascitic fluids were removed at intervals from day 28 to day 33. For mouse antisera raised to whole cells, S. frugiperda cells infected with YM1/19-5, YM1/10-2 or AcNPV were harvested 2 days post infection, washed twice in PBS and injected into mice. Each animal received $3 \times 10^6$ cells intraperitoneally on days 0 and 21 and the animals were terminally bled on day 42.

Immunoblotting. SDA-PAGE separated samples were subjected to electrophoretic transfer, for 3 hours at 0.8 mA/cm$^2$m onto Durapore membrane (Millipore Corp) using a semi-dry electroblotter (Satoblot II, Sartorius Corp). The blotted membrane was soaked overnight at 4° C. in blocking buffer (5% (w/v) skimmed milk, 0.5%(v/v) Tween-20 in PBS). The membrane was then treated for 90 minutes with the appropriate antisera diluted in blocking buffer and then washed with PBST (0.5%(v/v) Tween-20 in PBS). This was followed by treatment for 90 minutes with the appropriate anti IgC antiserum coupled to alkaline phosphatase (Sigma Chemical Co) before a final wash in PBST. Bound antibodies were detected using Fast BB salt and β-naphthyl) phosphate (Sigma Chemical Co.) as a substrate.

Plaque reduction neutralization tests. Antisera and BTV dilutions were done in PAS. 100 μl aliquots of diluted virus in 24-well tissue culture plates (Sterilin, Feltham, England) and incubated at 4° C. overnight. As controls normal sera or PAS alone were used. Then 0.5 ml of a suspension of Vero cells ($2\times10^5$ cells/ml in L15 medium supplemented with 2% (v/v) fetal calf serum) was added to each well and the plates were incubated at 35° C. for 4 hours. The cells were then overlaid with 0.75% (w/v) carboxymethyl cellulose in L15 medium. After incubation for four days at 35° C. the cells were fixed with 10% (v/v) formalin in PAS for 15 minutes and stained with 1.5% (w/v) crystal violet in 95%(v/v) ethanol for 15 minutes. Plaques in each well were then counted.

Construction of recombinant viruses (YM1/10-5, YM1/10-2) Baculovirus transfer vector pAcYM1/10-5 containing the entire sequence representing the BTV-10 M5 RNA segment was constructed according to the scheme in FIG. 1. The insert was completed at the 5' end, with an additional G nucleotide derived from pUC-4K, and the 3' end had 24 nucleotides missing (FIG. 2). Thus the transfer vector pAcYM1/19-5 contained the entire open reading frame coding for VP5 downstream of the AcNPV polyhedrin promotor. The orientation of the L2 DNA insert in relation to the polyhedrin promotor of pAcYM1/10-2 was determined by DNA sequence analysis (FIG. 2). In order to transfer the VP5 and the VP2 genes into the AcNPV genomes S. frugiperda cells were cotransfected with infectious AcNPV DNA and either pAcYM1/10-5 or pAcYM1/10-2 transfer vector DNA. Polyhedrin negative, recombinant progeny viruses were selected and after three plaque purifications high titer stocks ($10^8$p.f.u./ml) of two recombinant viruses, YM1/10-5 and YM1/10-2, were prepared on monolayers of S. frugiperda cells.

Figures 3, 4, 5:
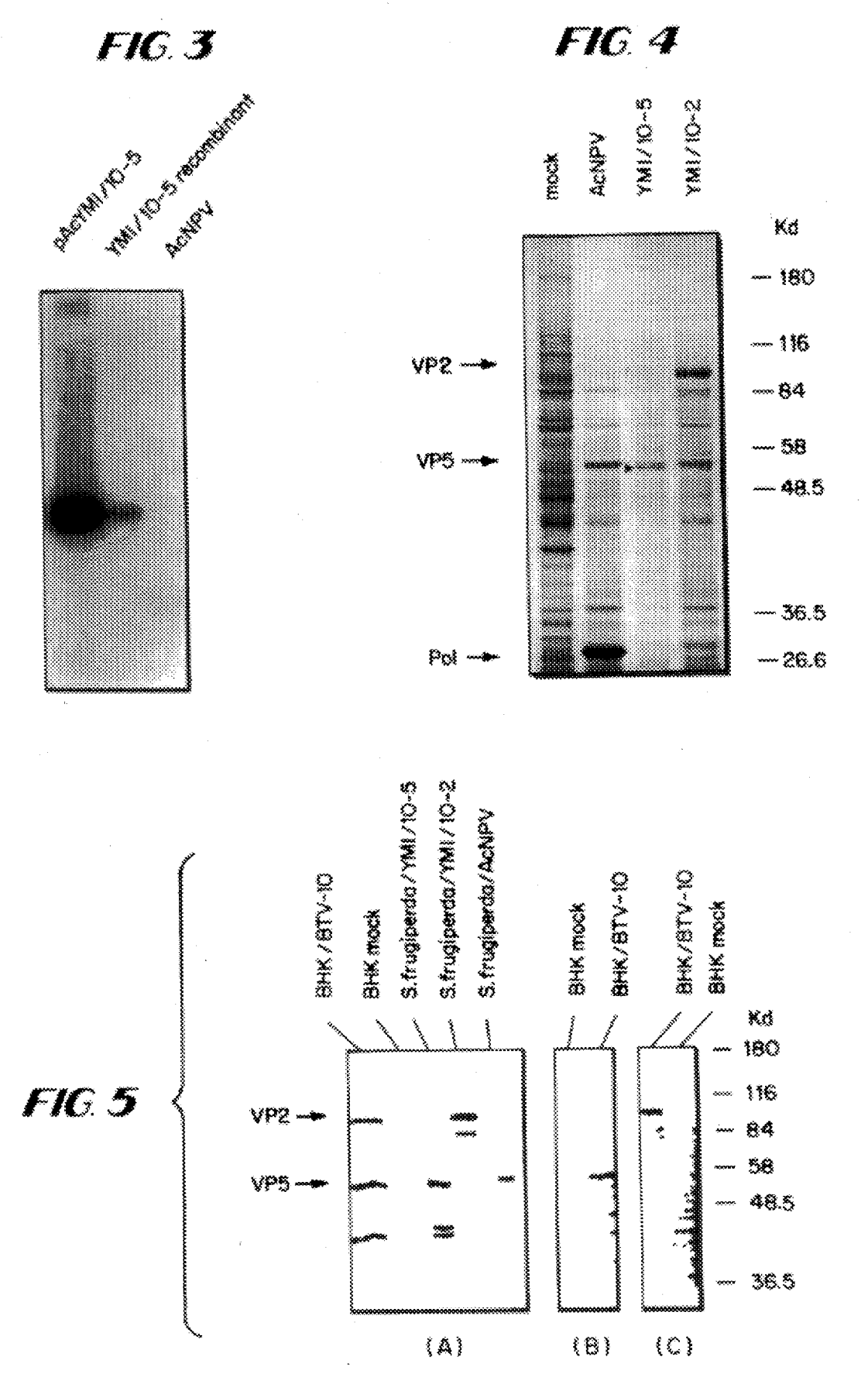

Analysis of recombinant viral DNA. In order to confirm the presence of DNA coding for VP5 and VP2 in the recombinant baculoviruses, DNA from YM1/10-5, YM1/10-2 and wild type AcNPV was isolated and subjected to Southern blot analysis. As shown in FIG. 3, both YM1/10-5 recombinant viral DNA and pAcYM1/10-5 transfer vector DNA, when digested with BamHI, both contained only one band of equal size that hybridized to the nick-translated segment 5 DNA probe. No bands were detected, under the same conditions, in the AcNPV viral DNA digested with BamHI. Southern analysis of BamHI digested YM1/10-2 viral DNA with nick-translated segment 2 DNA also confirmed the presence of segment 2 DNA in the YM1/10-2 recombinant baculovirus.

Expression of VP5 and VP2 in S. frugiperda cells

Infection of S. frugiperda cells with YM1/10-5 or YM1/10-2 did not produce visible nuclear inclusions. When extracts of these cells were run on a 10% SDS-PAGE gel and stained with Coomassie blue in each case an extra band was observed that was not present in mock or AcNPV infected cells (FIG. 4). In the case of YM1/10-5 the extra band corresponded to the expressed VP5 size of 59 Kd. For YM1/10-2 the expressed VP2 105 Kd was observed. Neither YM1/10-5 or YM1/10-2 infected cells produced the 29 Kd polyhedrin (Pol) band seen in AcNPV infected cells. Immunoblotting with rabbit antisera raised to BTV-10 showed that both the expressed recombinant VP5 and VP2 proteins were recognized and co-migrated with the authentic proteins in BTV-10 infected BHK cells (FIG. 5). In the case of the expressed VP2 the antisera recognized one major band of 105 Kd whilst in the case of the expressed VP5 the antisera recognized one band of 59 Kd and a number of other bands of lower molecular weight. The antisera did not recognize any proteins in AcNPV infected S. frugiperda cells.

Figure 6A:
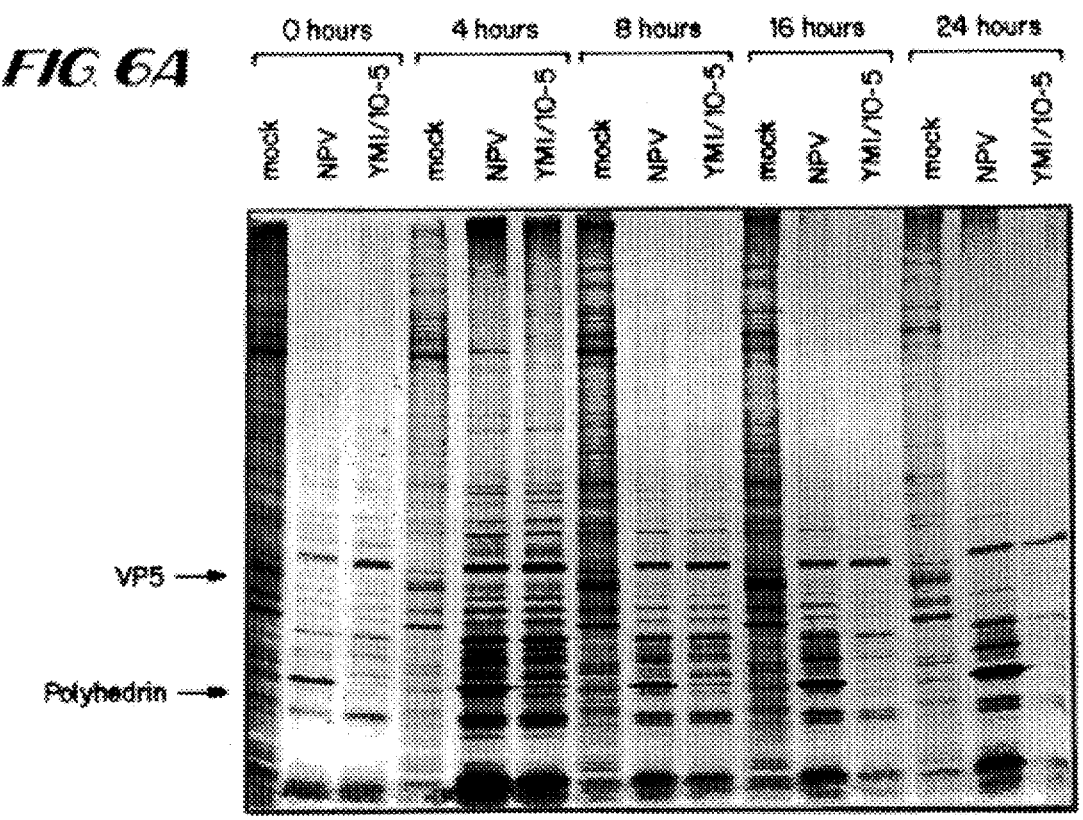
Figure 6B:
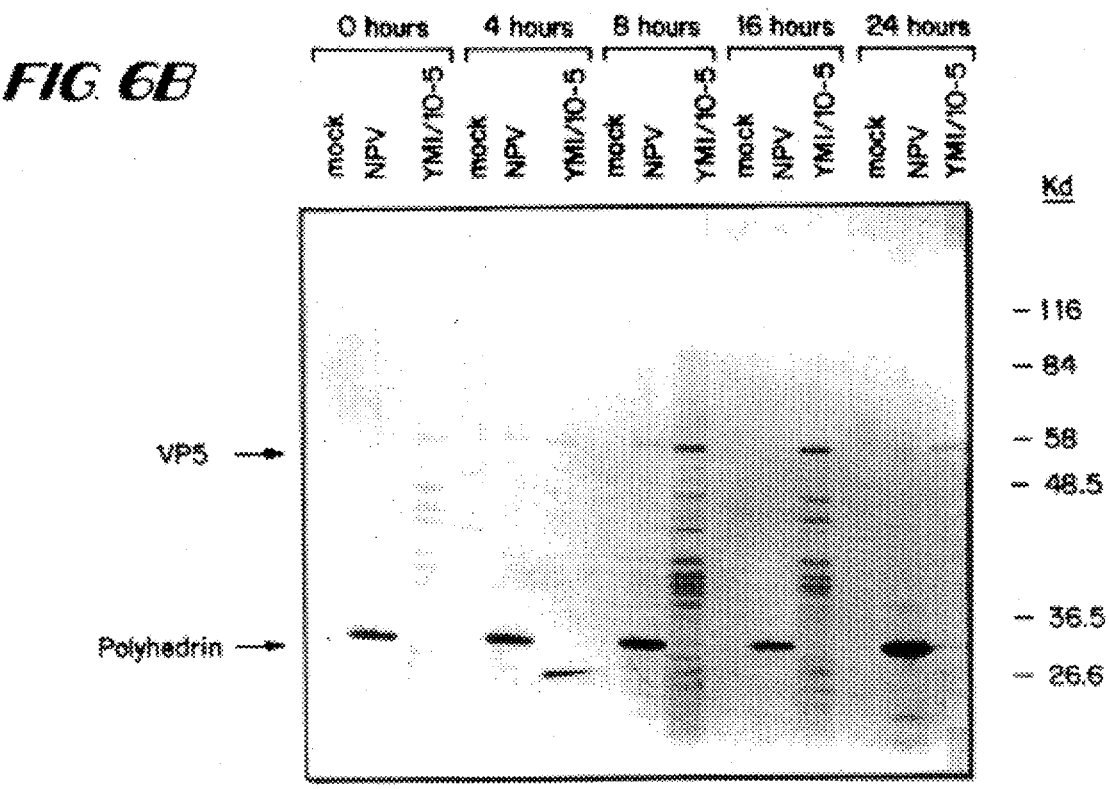

Both rabbit antisera raised to the expressed VP2 and mouse ascitic fluid raised to the expressed VP5 recognized the corresponding authentic proteins in BTV-10 infected BHK cells (FIG. 5), neither the preimmune rabbit sera or the control ascitic fluid recognized these proteins. To determine if the bands of less than 59 Kd seen on immunoblotting the expressed VP5 protein represented proteolytic degradation products or premature terminations of mRNA translation an immune precipitation of 35 S-methionine pulse-chase labelled YM1/10-5 infected S. frugiperda cells were undertaken. As shown in FIG. 6, rabbit antiserum raised to BTV-10 precipitated a band of 59 Kd from YM1/10-5, but not from mock or AcNPV, infected cells at all of the time points. A series of bands of molecular weights less than 59 Kd were also precipitated from only the YM1/10-5 infected cells. The intensity of these smaller bands increased up to 8 hours post-labelling and then decreased. The precipitation of a 29 Kd protein from AcNPV infected cells was probably due to the non-specific precipitation of polyhedral inclusion bodies (data not shown).

Neutralization of BTV by antisera raised to recombinant VP5 and VP2 Antisera were raised to recombinant VP5 and VP2 proteins purified by SDS-PAGE in mice and rabbits respectively. Antisera to whole S. frugiperda cells infected with YM1/10-5, YM1/10-2 or AcNPV were also raised in mice. All of these sera, along with preimmunce rabbit sera and control ascitic fluid, were tested for their ability to neutralize BTV in vitro by plaque reduction neutralization tests (Table 1). Rabbit antisera raised to VP2 had a neutralizing titer of greater than 1:640 against BTV-10 and greater than 1:160 against BTV-11 and BTV-17. The sera had not neutralizing activity against BTV-13.

Mouse ascitic fluid raised to the expressed VP5 had no neutralizing antibody titer to BTV-10, 11, 13 or 17. In the case of mouse antisera raised to whole S. frugiperda cells infected with either YM1/10-2, YM1/10-5 or AcNPV four mice were immunized, and tested for each condition. The mean neutralization titers for YM1/10-2 and YM1/10-5 infected cells was 1:205 and 1:51 respectively. The mean titer for AcNPV infected cells was 1:55 and the neutralization titer induced by YM1/10-2 infected cells was significantly greater than this, as judged by the two sample t-test, whilst the neutralization titer of the sera raised to YM1/10-5 infected cells was not.

TABLE 1

Plaque reduction neutralization titers of antisera to expressed VP2 and VP5

| Antisera | BTV Serotypes | | | |
|---|---|---|---|---|
| | 10 | 11 | 13 | 17 |
| Rabbit VP2 antisera | >640 | >160 | 0 | >160 |
| Preimmune rabbit sera | 0 | 0 | 0 | 0 |
| Mouse VP5 ascitic fluid | 0 | 0 | 0 | 0 |
| Control ascitic fluid | 0 | 0 | 0 | 0 |

Mouse antisera to:
YM1/10-2 infected
S. frugiperda cells 205 ± 74*
(n = 4)
YMI1/10-5 infected
S. frugiperda cells 51 ÷ 23+

TABLE 1-continued (n = 4)
AcNPV infected
S. frugiperda cells 51 + 40
(n = 4)

*Significantly different from AcNPV infected S. frugiperda cells at the P = 0.05 level.
+Not significantly different from AcNPV infected S. frugiperda cells at the P = 0.05 level.

Recombinant baculoviruses have been constructed than contain DNA sequences coding for the BTV-10 proteins VP5 and VP2 downstream of the polyhedrin promoter. When S. frugiperda cells are infected with these recombinants VP5 and VP2 proteins are synthesized to a high level in place of the polyhedrin protein. The expression of VP5 is not to as high level as that of VP2 as judged by Coomassie blue staining SDS-PAGE gels. This would appear to be at least partially due to proteolytic degradation since immunoblotting of the expressed proteins revealed a series of immunologically related species, of lower molecular weights, in the case of VP5 but not for VP2. That these species represent post-translational proteolytic degradation rather than premature terminations of translation is supported by the observation that immune precipitation of 35S methionine pulse labelled YM1/10-5 infected S. frugiperda cell extracts showed that the degraded species increased in amount with the post-labelling chase period. Both the expressed VP5 and VP2 were recognized by antiserum raised to BTV-10 virus and antisera raised to these expressed proteins recognized authentic BTV-10 VP2 and VP5. Thus it would appear that the baculovirus expressed proteins have immunological properties closely related to the authentic BTV-10 proteins. This is corroborated by the fact that the expressed VP2 could induce neutralizing antibodies.

The use of an improved baculovirus transfer vector pAcYM1 (Matsuura et al, 1987) gave higher levels of expression of VP2 in baculovirus, and induced higher titers of neutralizing antibodies than previously reported for the transfer vector pAcRP6S (Inumari and Roy, 1987). Expressed VP2 also induced neutralizing antibodies to BTV-11 and BTV-17 but not BTV-13, albeit at a lower titer than to BTV-10, and this pattern of cross-serotype neutralization reflects the pattern of homologies between the VP2 proteins of the various serotypes (Yamaguchi et al, 1988). The use of SDS-PAGE purified expressed VP2 as an antigen was successful in inducing neutralizing antibodies which was not the case for VP2 isolated in the same manner from BTV virions. In contrast to these data the expressed VP5 protein purified by SDS-PAGE did not induce neutralizing antibodies against BTV-10. Immunization of mice with whole S. frugiperda cells infected with YM1/10-5 recombinant also failed to induce neutralizing antibodies but immunization with cells infected with the YM1/10-2 recombinant did induce neutralizing antibodies. Therefore the purification of the expressed proteins by SDS-PAGE did not appear to interfere with their ability to induce neutralizing antibodies. The data presented indicates that the outer capsid protein VP2 plays a direct role in neutralization of BTV whilst VP5 does not.

Vaccine Assessments

Experiments were carried out to assess the effectiveness of various recombinant polypeptide and combinations as vaccines for eliciting a protective effect in sheep against BTV-10. Comparisons were made between antigens extracted from native virus and recombinant polypeptide. The results are given in Table 2.

From the results it can be seen that soluble VP2 from purified BTV virus appeared to be negative whereas all sheep that had received polypeptide produced in insect cells by recombinant baculovirus were solidly protected. Particularly high level of protection were observed in sheep that had received a combination of recombinant VP2 and VP5.

TABLE 2

| ANTIGEN | ADJU-VANT | INOCULATIONS | | | SERUM NEUTRALIZATION TITERS AGAINST BTV-10 | | | | | | | | CLINICAL REACTION INDEX (CRI) |
|---|---|---|---|---|---|---|---|---|---|---|---|---|---|
| | | 14/12/88 | 4/1 | 25/1 | 18/1 | 25/1 | 31/1 | 3/2 | 6/2 | 13/2 | 20/2 | 27/2 | |
| BTV-10VP2 | − | ✓ | ✓ | ✓ | 32 | 32 | 64 | 64 | 32 | 64 | 16 | 8 | 7 |
| 250–500 µg | − | ✓ | ✓ | ✓ | 32 | 32 | 32 | 32 | 16 | 8 | 8 | 4 | 1,4 |
| | + | ✓ | ✓ | ✓ | 16 | 16 | 32 | 32 | 32 | 16 | 12 | 8 | 0,0 |
| | + | ✓ | ✓ | ✓ | <4 | 4 | 16 | 16 | 16 | 8 | 8 | 8 | 3,1 |
| BTV-10/11/17VP2 | − | ✓ | ✓ | ✓ | <4 | 4 | 16 | 16 | 16 | 8 | 8 | 8 | 0,0 |
| | − | ✓ | ✓ | ✓ | 16 | 16 | 64 | 64 | 32 | 32 | 16 | 612 | 0,0 |
| | + | ✓ | ✓ | ✓ | 16 | 16 | 32 | 32 | 32 | 16 | 12 | 8 | 0,0 |
| | + | ✓ | ✓ | ✓ | 8 | 16 | 32 | 32 | 32 | 7 | 16 | 12 | 0,0 |
| BTV-10VP2 & VP5 | − | ✓ | ✓ | ✓ | <4 | <4 | 16 | 8 | 8 | 8 | 4 | 4 | 0,0 |
| | − | ✓ | ✓ | ✓ | <4 | 4 | 16 | 8 | 8 | 8 | 7 | 4 | 0,0 |
| | + | ✓ | ✓ | ✓ | >32 | 128 | 512 | 256 | 128 | 128 | 128 | 96 | 0,0 |
| | + | ✓ | ✓ | ✓ | 32 | 64 | 128 | 128 | 64 | 32 | 32 | 24 | 0,0 |
| BTV-10VP1,VP2,VP3, | − | ✓ | ✓ | ✓ | 8 | <4 | 8 | 8 | 8 | 16 | 16 | 16 | 0,0 |
| VP5,VP6,VP7,NS1, | − | ✓ | ✓ | ✓ | 16 | 4 | 8 | 8 | 8 | 24 | 24 | 12 | 0,0 |
| NS2,NS3 | + | ✓ | ✓ | ✓ | >32 | 128 | 256 | 256 | 128 | 64 | 64 | 16 | 0,0 |
| | + | ✓ | ✓ | ✓ | >32 | 64 | 128 | 128 | 64 | 64 | 48 | 24 | 0,0 |
| 8TV-10VP2 | − | ✓ | ✓ | ✓ | >32 | 64 | 16 | 16 | 16 | 16 | 7 | 8 | 0,0 |
| 500–1000 µg | − | ✓ | ✓ | ✓ | >32 | 64 | 32 | 32 | 16 | 16 | 12 | 8 | 0,0 |
| | + | ✓ | ✓ | ✓ | 32 | 32 | 16 | 16 | 16 | 8 | 6 | 4 | 0,0 |
| | + | ✓ | ✓ | ✓ | 16 | 8 | <4 | <4 | <4 | 7 | >4 | >4 | 0,0 |
| BTV-10VP2 | − | ✓ | ✓ | ✓ | >32 | 128 | 32 | 32 | 32 | 16 | 16 | 8 | 0,0 |
| 1000–2000 µg | − | ✓ | ✓ | ✓ | >32 | 64 | 16 | 16 | 16 | 16 | 8 | 8 | 0,0 |
| | + | ✓ | ✓ | ✓ | >32 | 128 | 64 | 64 | 32 | 32 | 32 | 16 | 0,0 |
| | + | ✓ | ✓ | ✓ | >32 | 512 | 128 | 128 | 128 | 64 | 64 | 32 | 0,0 |
| SOLUBILIZED | + | ✓ | ✓ | ✓ | <4 | <4 | <4 | <4 | <4 | >4 | <4 | <4 | 4,6 |
| BTV-10VP2 | + | ✓ | ✓ | ✓ | <4 | <4 | <4 | <4 | <4 | >4 | <4 | <4 | 5,1 |

TABLE 2-continued

| ANTIGEN | ADJU-VANT | INOCULATIONS | | | SERUM NEUTRALIZATION TITERS AGAINST BTV-10 | | | | | | | | CLINICAL REACTION INDEX |
| --- | --- | --- | --- | --- | --- | --- | --- | --- | --- | --- | --- | --- | --- |
| | | 14/12/88 | 4/1 | 25/1 | 18/1 | 25/1 | 31/1 | 3/2 | 6/2 | 13/2 | 20/2 | 27/2 | (CRI) |
| SALINE | − | ✓ | ✓ | ✓ | <4 | <4 | <4 | <4 | <4 | >4 | <4 | <4 | 6,0 |
| | − | ✓ | ✓ | ✓ | <4 | <4 | <4 | <4 | <4 | >4 | <4 | <4 | 7,4 |
| | + | ✓ | ✓ | ✓ | <4 | <4 | <4 | <4 | <4 | >4 | <4 | <4 | 3,7 |
| | + | ✓ | ✓ | ✓ | <4 | <4 | <4 | <4 | <4 | >4 | <4 | <4 | 5,0 |

Example 2

This example describes the production of antigenitally active particles comprising bluetongue proteins Bt VP2, VP3, VP5 and VP7.

A. VP2/VP5 Construct

Figure 7:
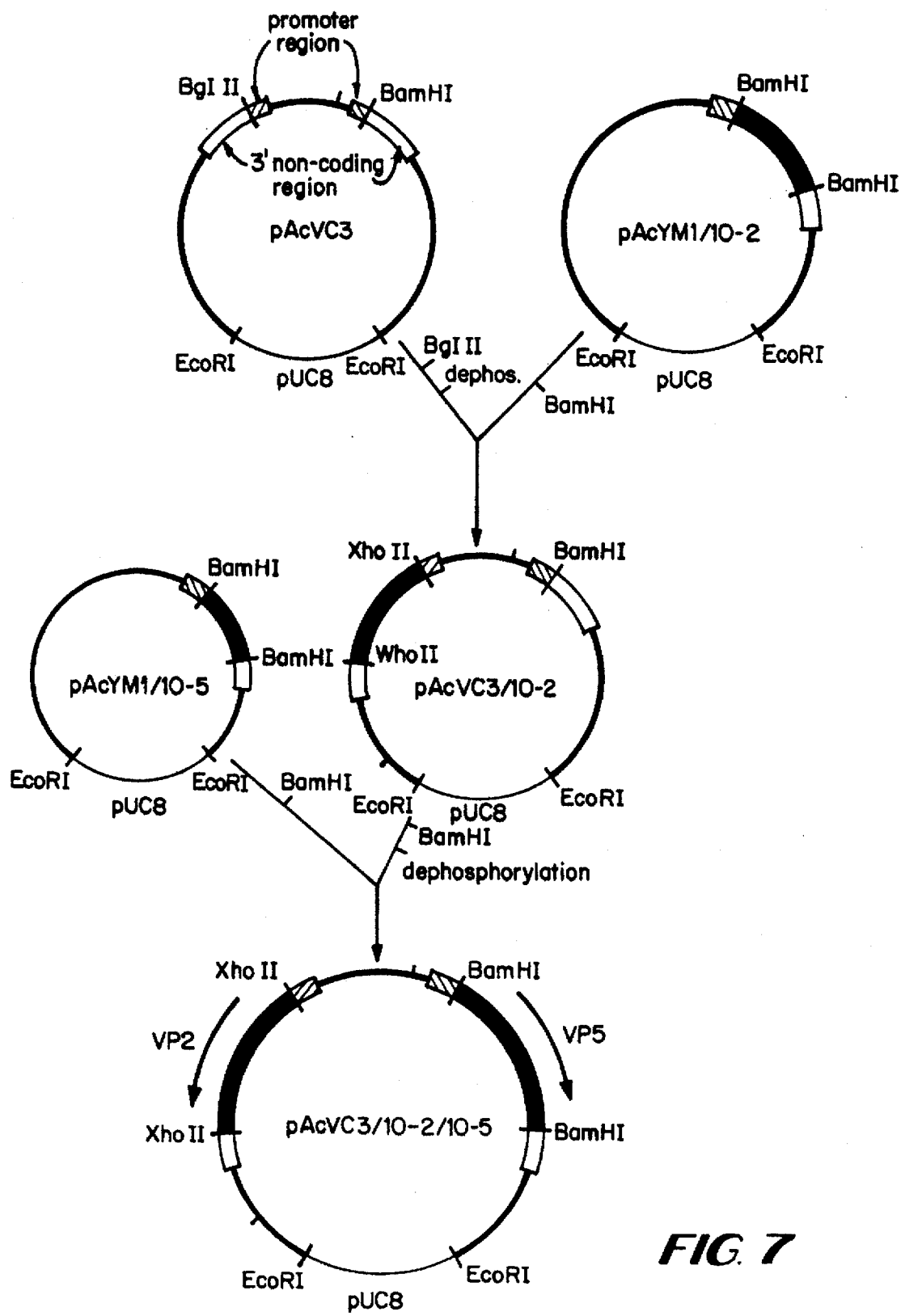
Figure 8A:
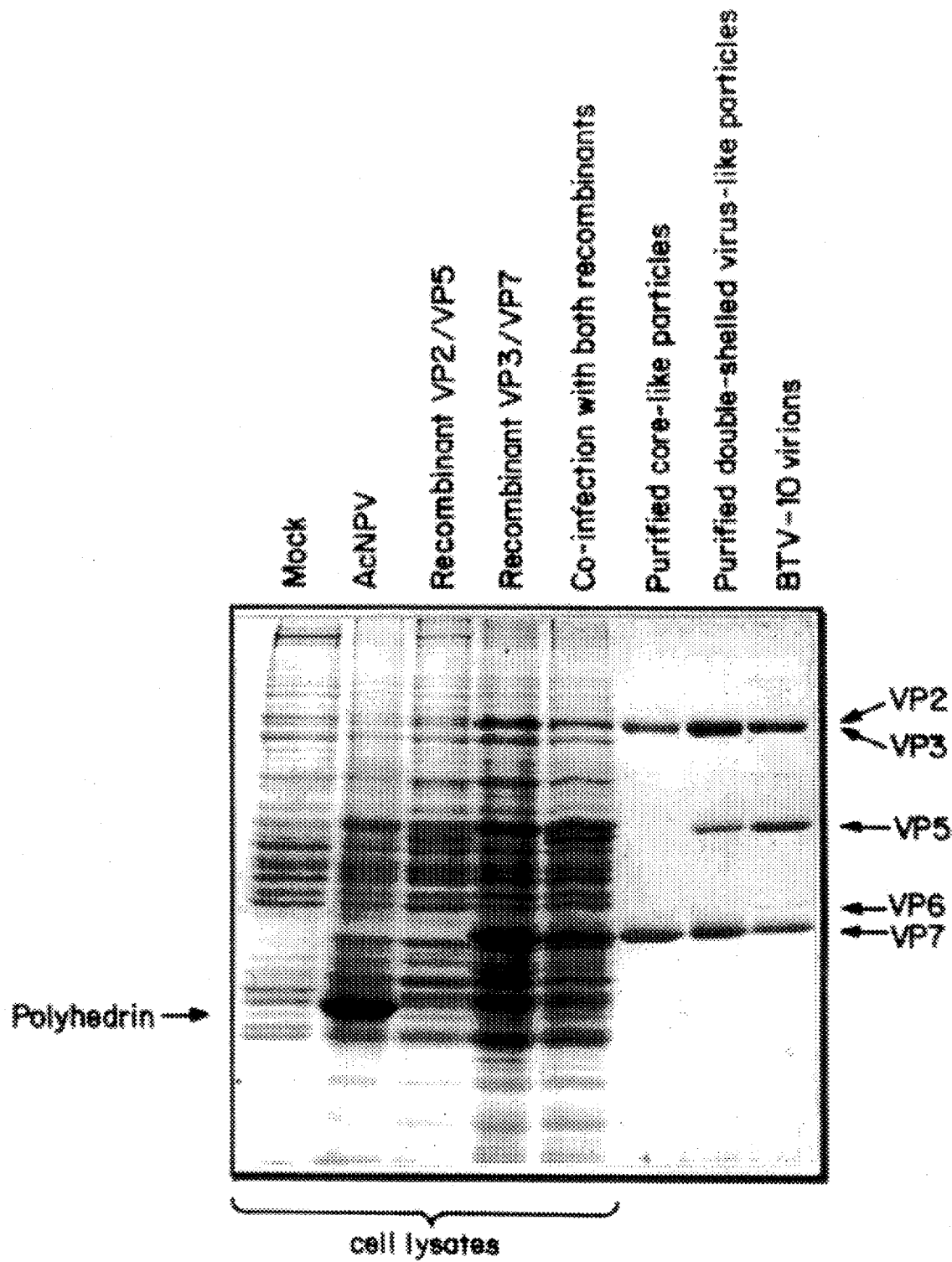

A VP2-VP5 recombinant plasmid was constructed by the manipulations shown in FIG. 7. They involved excision of the L2 and M5 genes from their PAcYM1 single expression transfer vectors and insertion into the BamHI and BglII sites (respectively) of the multiple expression vector pAcVC3. Recombinant baculoviruses were prepared by the established procedure of co-transfecting *S. frugiperda* insect cells with the recombinant plasmid DNA and infectious wild-type AcNPV DNA. Progeny viruses were titrated using confluent monolayers of *S. frugiperda* cells and putative recombinants were selected on the basis of their polyhedrin-negative phenotype (ca 0.1% frequency). After successive rounds of plaque purification, a high titre vital stock was prepared. *S. frugiperda* cells infected with the recombinant baculovirus synthesized two unique protein species in plate of the 29 KDa polyhedrin protein seen in wild-type AcNPV infected cells (FIG. 8A).

The sizes of the expressed proteins agree with those expected or VP2 and VP5 calculated from their amino acid compositions (i.e. 111, 112 Da and 59.136 Da respectively).

Figure 8B:
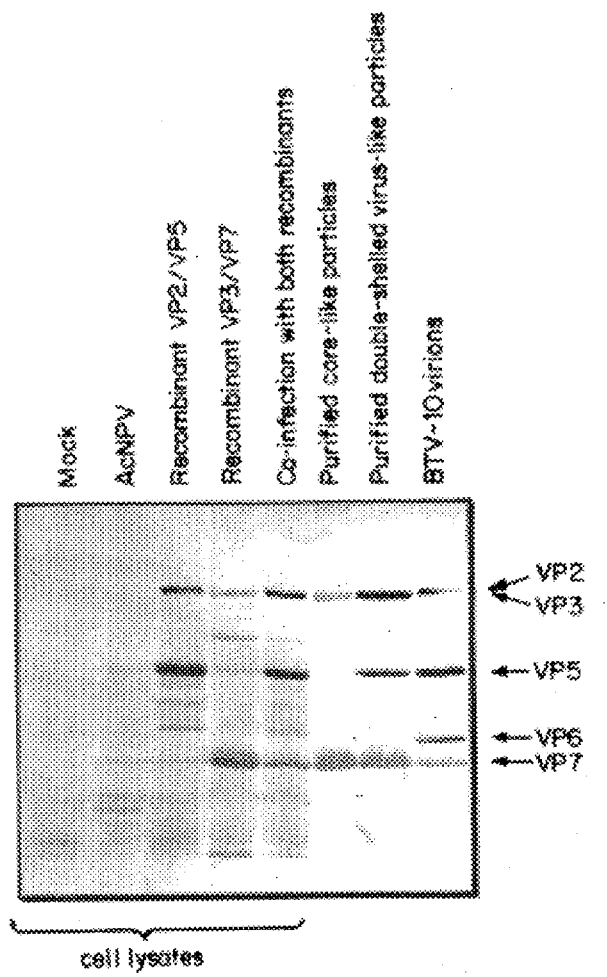

Since the levels of expression were below that which could be determined by staining, confirmation that the expressed proteins represented authentic BTV proteins was provided by Western blot analyses using antisera raised to BTV-10 virus particles (FIG. 8B).

B. VP3/VP7 Construct

Figure 9A:
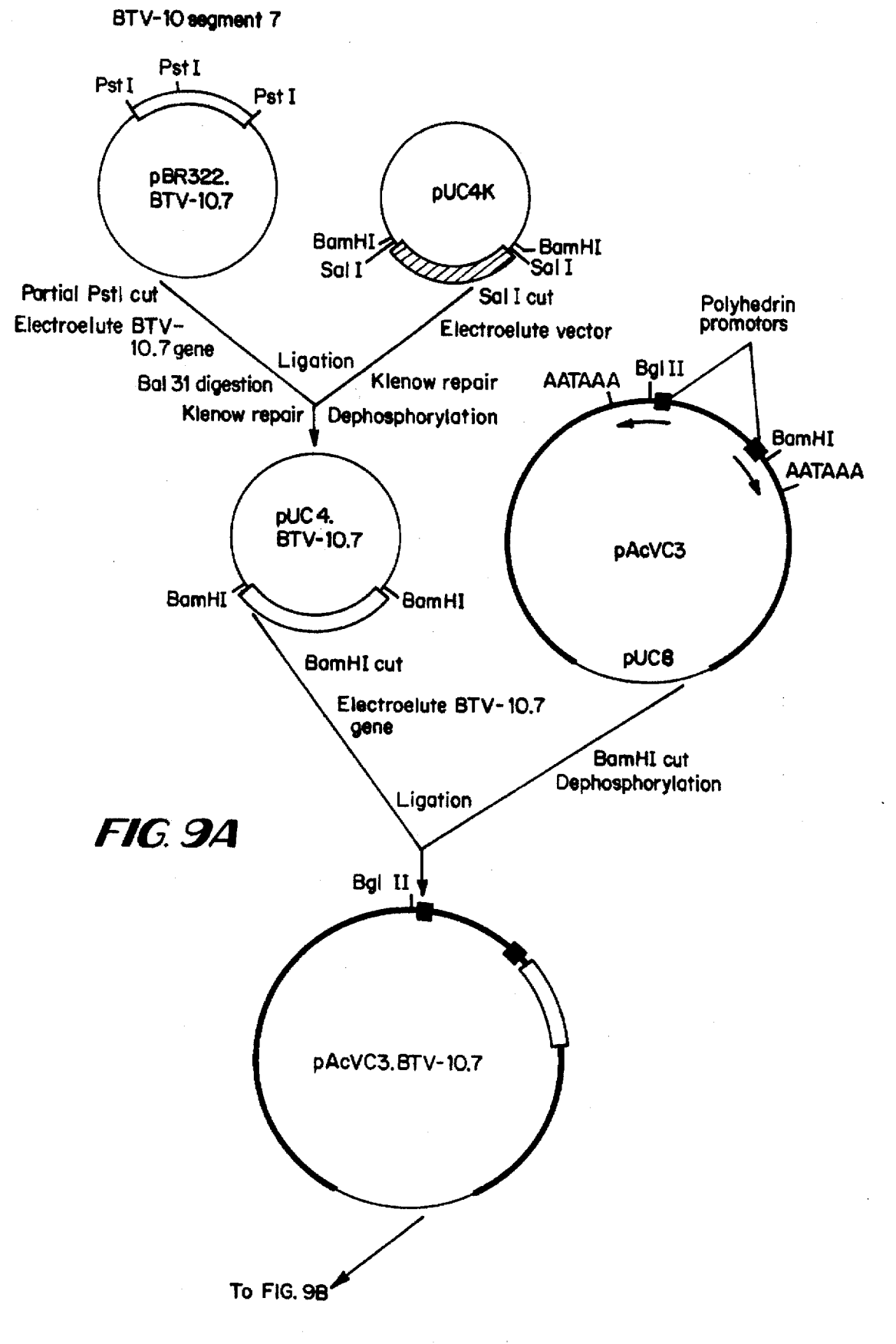
Figure 9B:
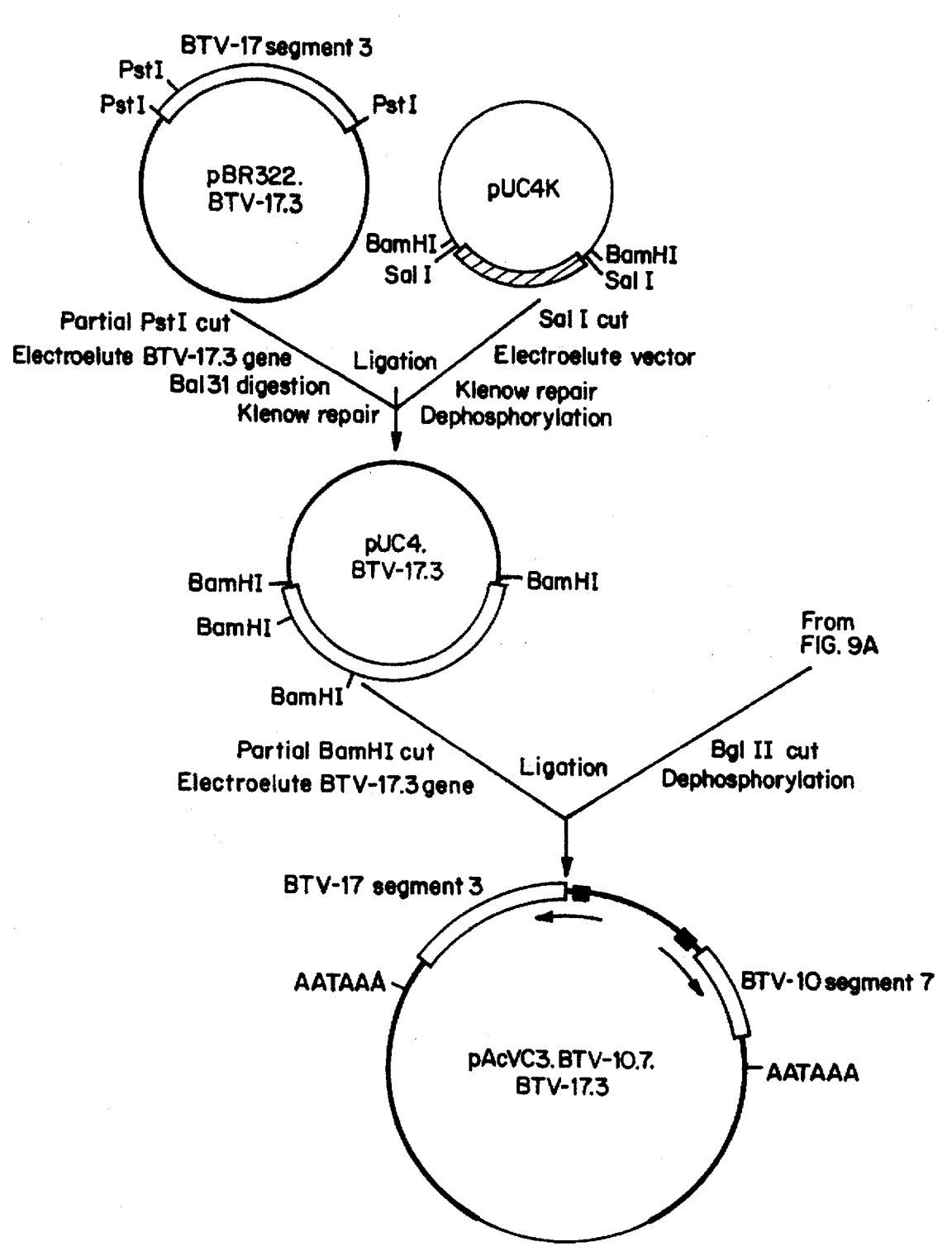

The construction of recombinant expression vector pAcVC3, BTV-10.7, BTV-17.3 is illustrated in FIG. 9.

The initial step for the expression of the BTV genes was to synthesize cDNA copies of the double stranded RNA L3 and M7 segments. Although these were isolated from different serotypes (17 amd 10 respectively), the L3 gene is very highly conserved with an amino acid homology of greater than 99%.

Homopolymeric tails introduced to aid the cloning procedure were removed by limited Bal31 exonuclease digestion before insertion of the genes into the pAcVc3 transfer vector. Recombinant baculoviruses were prepared by the established procedure of co-transfecting *S. frugiperda* cells with the dual expression plasmid DNA and wild-type AcNPV DNA.

Progeny viruses were titrated using confluent monolayers of *S. frugiperda* cells and putative recombinants selected on the basis of their polyhedrin negative phenotype (ca 0.1% frequency). After successive rounds of plaque purification of high titre viral stock was prepared. *S. frugiperda* cells infected with the recombinant baculovirus synthesized two unique proteins species in place of the 29 kDa polyhedrin protein seen in wild-type AcNPV infected cells (FIG. 10A).

The sizes of the expression proteins agree with those expected for VP3 and VP7 calculated from their amino acid compositions (103,226 KDa and 385,48 KDa respectively). Confirmation that these expressed proteins represented authentic BTV proteins was provided by Western blot analysis with antisera raised to BTV-10 virus particles (FIG. 10B).

C. Dual Expression of VP2/VP5 and VP3/7 Constructs

To assess the interaction of these proteins with the BTV core-like particles, insect cells were co-infected with both dual recombinant baculoviruses (in order to co-express VP2, VP3, VP5 and VP7).

Figure 11A:
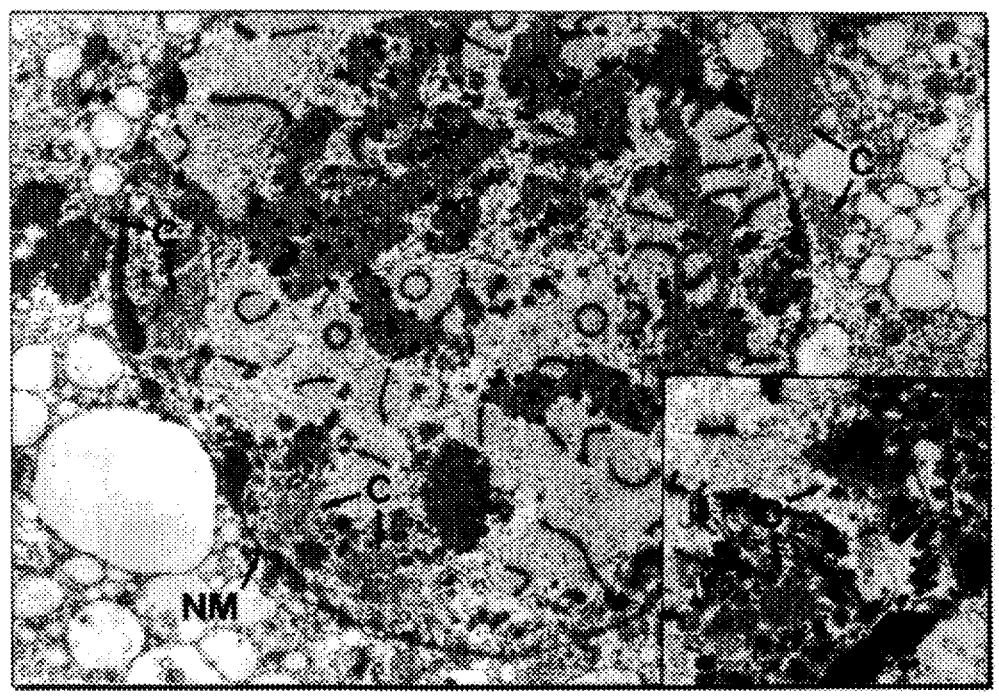
Figure 11B:
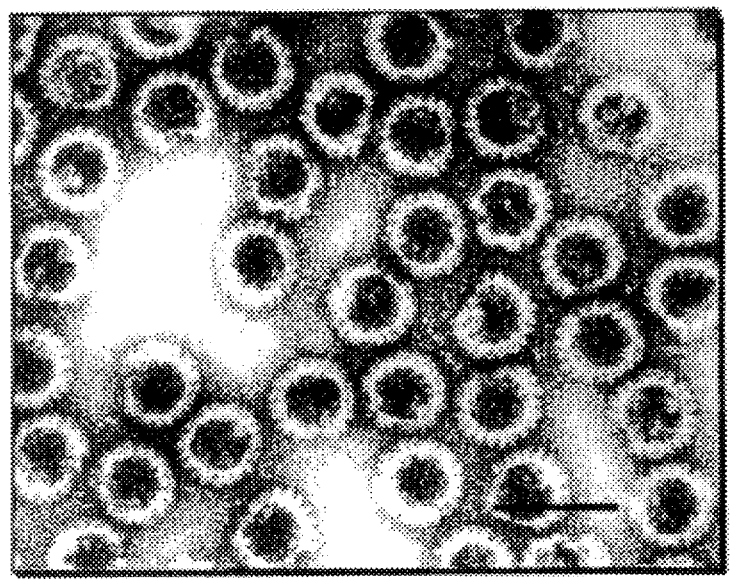
Figure 11C:
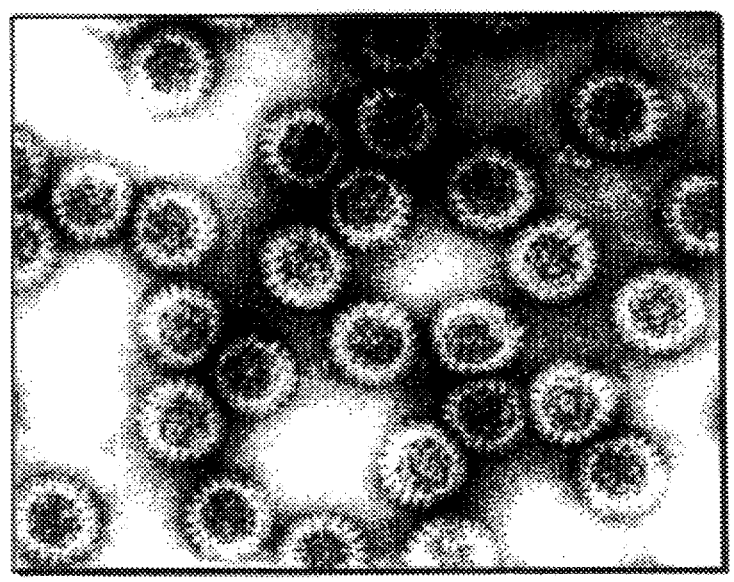
Figure 12A:
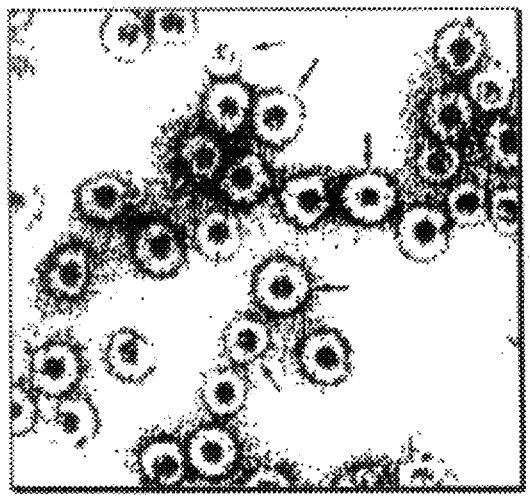
Figure 12B:
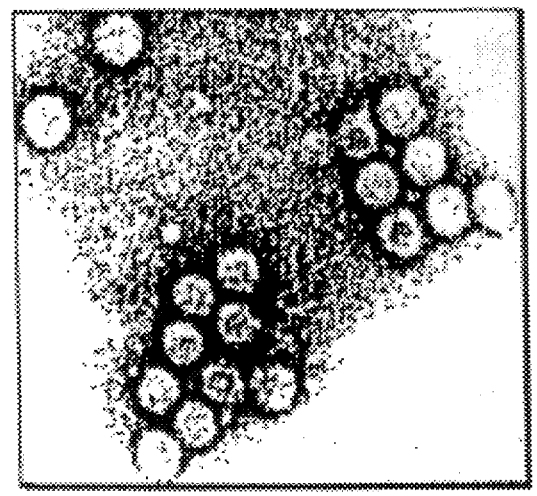
Figure 12C:
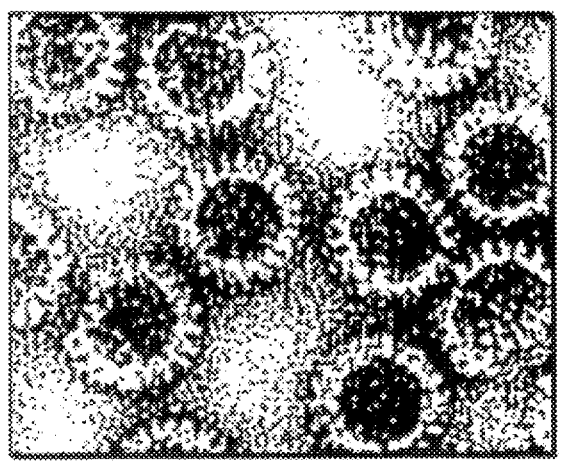
Figure 12D:
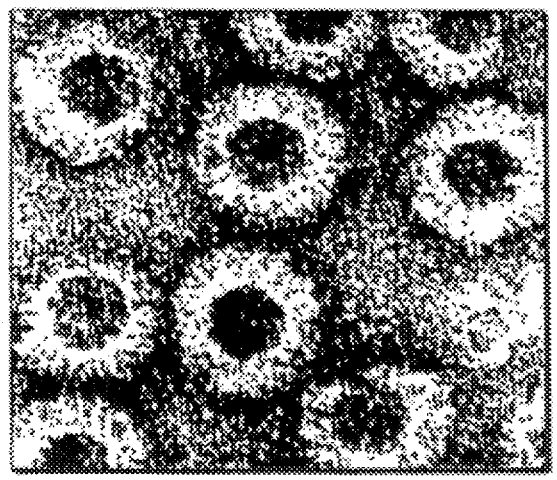
Figure 13:
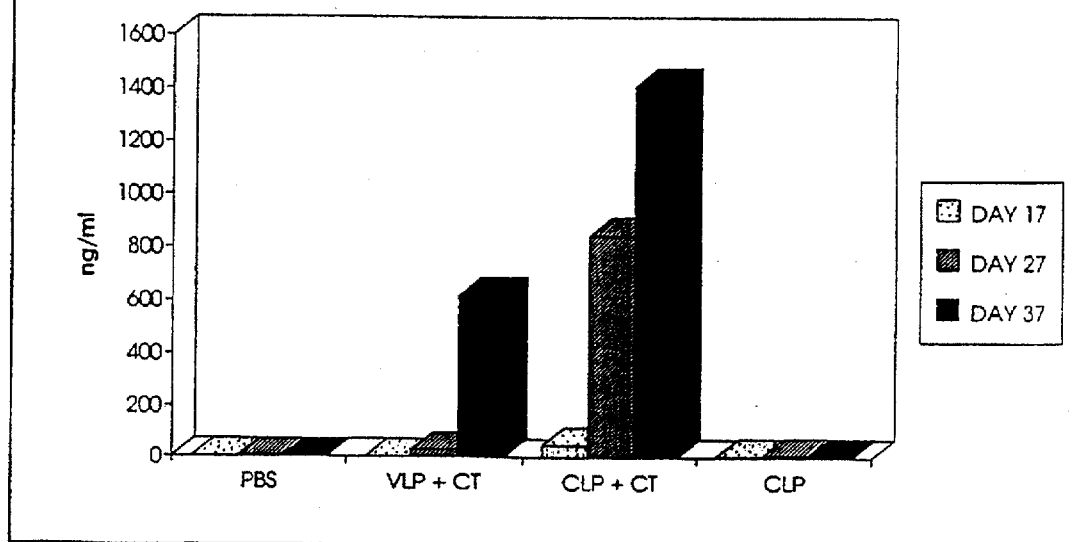
Figure 14:
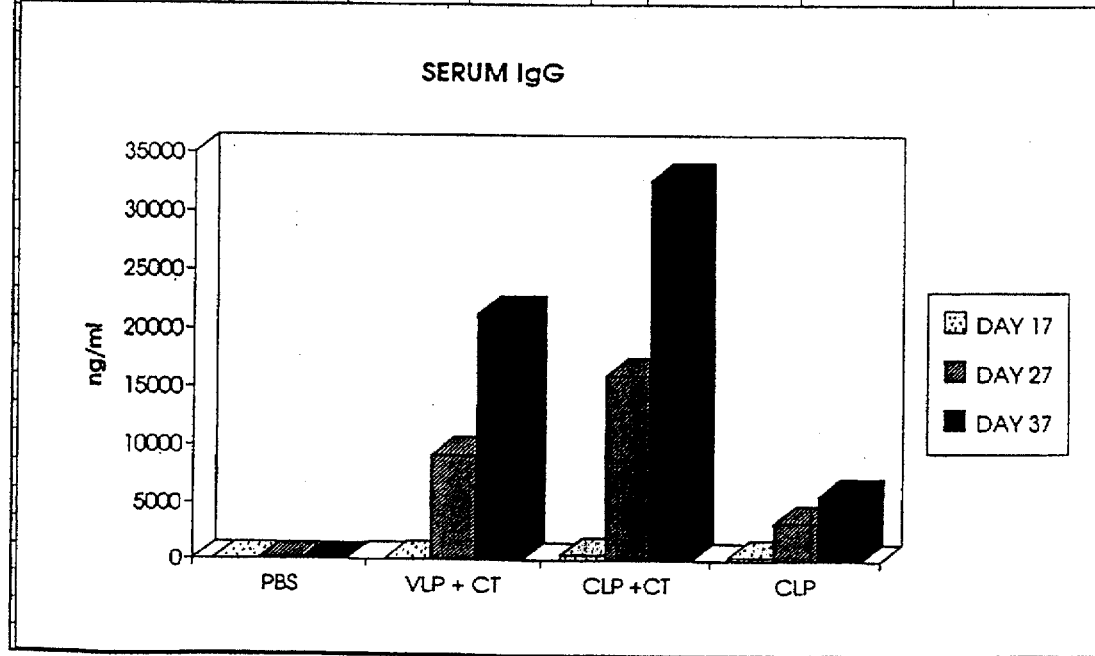
Figure 15:
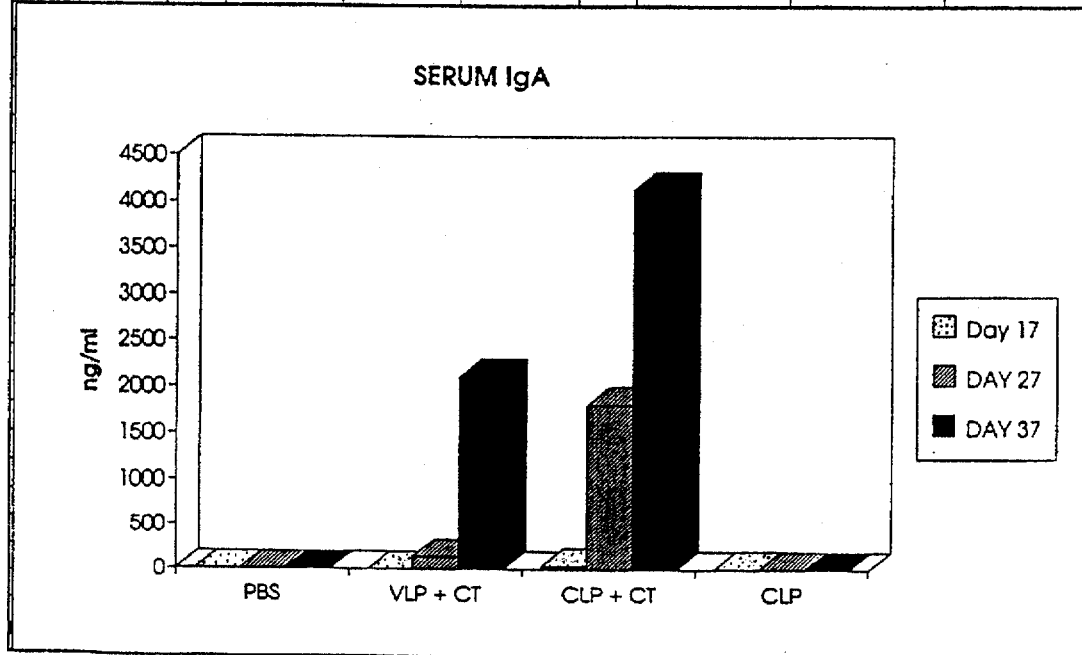

The cells were harvested at 48 hours post-infection, lysed with the non-ionic detergent Nonidet P40, and particles purified to homogeneity by centrifugation on discontinuous sucrose gradients. When examined under the electron microscope, empty double-shelled particles were observed consisting of a core surround by a thick outer capsid (FIG. 11A, large arrow). The diameters of the largest particles were also observed in the preparation (FIG. 11A, thin arrows). Their diameters were estimated to be of the order of 85 rim. A range of intermediate structures were also observed, apparently with varying amounts of the outer capsid proteins attached.

Figure 8C:
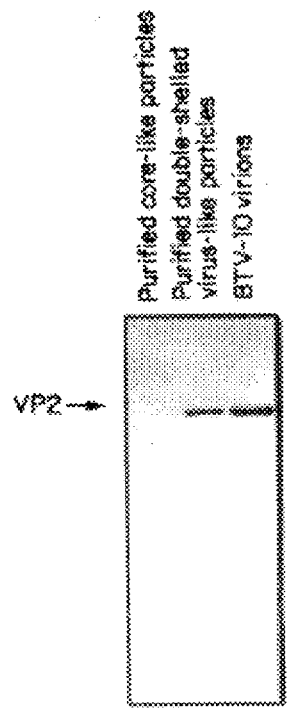

These may reflect different stages in particle assembly. Interestingly, the center areas of both types of particles (cores and virus-like particles) exhibited an icosahedral configuration. The smaller size of the central area of the virus-like particles is presumably due to the presence and density of the outer capsid proteins. The icosahedral configuration of the center was also apparent in several authentic BTV particles where stain had penetrated the particles. The purified expressed particles were analyzed by SDS-PAGE and Western Immunoblot and shown to contain large amounts of VP2 and VP5 (FIG. 8), in addition to VP3 and VP7.

The authenticity of the expressed empty double-shelled virus particles was assessed by their immunogenicity and haemagglutinating activity. Guinea pig sera raised against purified core-like particles and double-shelled virus-like particles were tested for their neutralizing activity against BTV-10. As expected, sera raised to the cores exhibited no neutralizing activity while in a 50% plague reduction test substantial neutralization was demonstrated by the sera raised to the double-shelled particles at a dilution of 1:10, 000. Monospecific sera raised to VP2 gave titers of <500. Purified double-shelled particles also exhibited haemagglutinating titers (Table 3), comparable to those observed with authentic virus. Purified core did not haemagglutinate. VP2 has been demonstrated to be the haemagglutinating protein in authentic bluetongue virus.

These data are supported by the inhibitory effect of monospecific sera raised to VP2 on the haemagglutination activity of the double-shelled particles. Monospecific sera raised to the other component proteins (VP3, VP5 and VP7) had essentially no effect (Table 3). Unlike authentic BTV, the virus-like particles were non-infectious when assayed in mammalian cells.

Several interesting conclusions regarding BTV morphogenesis can be drawn from the results described. The outer capsid proteins VP2 and VP5 do not attach individually to the core-like particles. This suggests that these proteins may interact before attaching to the core, or alternatively they may bind sequentially until a complete particle is produced. As with the formation of core-like particles in insect cells, the addition of theouter capsid is not dependent on the presence of the BTV non-structural proteins (NS1, NS2, NS3), or viral double-standard RNA, or the minor proteins VP1, VP4, VP6.

TABLE 3

Haemagglutination analysis of BTV double-shelled virus-like particles

| Substrate | Haemagglutination titer |
|---|---|
| Single-shelled CLP's | <2 |
| Double-shelled VLP's | 2048 |

| Sera Tested | Haemagglutination-Inhibitor titer |
|---|---|
| Preimmune rabbit | 16 |
| Rabbit anti VP2 | >1024 |

TABLE 3-continued

| Rabbit anti VP7 | 2 |
|---|---|
| Preimmune mouse | 4 |
| Mouse anti VP5 | 8 |
| Mouse anti VP3 | 32 |

*S. frugiperda* cells infected with the appropriate recombinant baculoviruses were lysed with Nonidet P-40 and double-shelled virus-like particles, or core-like particles were isolated on discontinuous sucrose gradients, the haemagglutination titer of this material was assayed at 4° C. using 0.25% rabbit erythrocytes as the indicator. Titers are expressed as the reciprocal of the highest serial dilution that gave complete haemagglutination. Antisera raised to baculovirus expressed BTV proteins were used in haemagglutination-inhibition tests. The inhibition titers are expressed as the reciprocal of the highest serial dilution of sera that gave complete inhibition of haemagglutination.

D. Vaccine Assessments

Additional experiments were carried out to assess the effectiveness of various recombinant polypeptide and combinations as vaccines for eliciting a protective effect in sheep against BTV-10. The results are given in Tables 4 and 5.

TABLE 4

Serum plaque reduction titers of sheep inoculated with recombinant BTV antigens

| GROUP NO. | ANTIGENS | SHEEP NO. | ADJU-VANT | INOCULATION (Day) | | | *SERUM NEUTRALIZATION TITERS AGAINST BTV-10 (Days) | | | | | | | |
|---|---|---|---|---|---|---|---|---|---|---|---|---|---|---|
| | | | | 0 | 21 | 42 | 25 | 42 | 48 | 50 | 52 | 60 | 67 | 74 |
| I | VP2: ~50 µg | 1 | − | ✓ | ✓ | ✓ | 32 | 32 | 64 | 64 | 32 | 64 | 16 | 8 |
| | | 2 | − | ✓ | ✓ | ✓ | 32 | 32 | 32 | 32 | 16 | 8 | 8 | 4 |
| | | 3 | + | ✓ | ✓ | ✓ | 16 | 16 | 32 | 32 | 32 | 16 | 12 | 8 |
| | | 4 | + | ✓ | ✓ | ✓ | <4 | 4 | 16 | 16 | 16 | 8 | 8 | 8 |
| II | VP2: ~100 µg | 5 | − | ✓ | ✓ | — | >32 | 64 | 16 | 16 | 16 | 16 | 8 | 8 |
| | | 6 | − | ✓ | ✓ | — | >32 | 64 | 32 | 32 | 16 | 16 | 12 | 8 |
| | | 7 | + | ✓ | ✓ | — | 32 | 32 | 16 | 16 | 16 | 8 | 6 | 4 |
| | | 8 | + | ✓ | ✓ | — | 16 | 8 | <4 | <4 | <4 | <4 | <4 | <4 |
| III | VP2: ~200 µg | 9 | − | ✓ | ✓ | — | >32 | 128 | 32 | 32 | 32 | 16 | 16 | 8 |
| | | 10 | − | ✓ | ✓ | — | >32 | 64 | 16 | 16 | 16 | 16 | 8 | 8 |
| | | 11 | + | ✓ | ✓ | — | >32 | 128 | 64 | 64 | 32 | 32 | 32 | 16 |
| | | 12 | + | ✓ | ✓ | — | >32 | 512 | 128 | 128 | 128 | 64 | 64 | 32 |
| IV | VP2: ~50 µg | 13 | − | ✓ | ✓ | ✓ | <4 | <4 | 16 | 8 | 8 | 8 | 4 | 4 |
| | VP5: ~20 µg | 14 | − | ✓ | ✓ | ✓ | <4 | 4 | 16 | 8 | 8 | 8 | 4 | 4 |
| | | 15 | + | ✓ | ✓ | ✓ | >32 | 128 | 512 | 256 | 128 | 128 | 128 | 96 |
| | | 16 | + | ✓ | ✓ | ✓ | 32 | 64 | 128 | 128 | 64 | 32 | 32 | 24 |
| V | VP1,CP5: (~20 µg, each) | 17 | − | ✓ | ✓ | — | 8 | >4 | 8 | 8 | 8 | 16 | 16 | 16 |
| | VP2;VP3: (~50 µg, each) | 18 | − | ✓ | ✓ | — | 16 | 4 | 8 | 8 | 8 | 24 | 24 | 12 |
| | VP6,VP7: (~100 µg, each) | 19 | + | ✓ | ✓ | — | >32 | 128 | 256 | 256 | 128 | 64 | 64 | 16 |
| | NS1;NS2: (~200 µg, each) NS3: (~20 µg) | 20 | + | ✓ | ✓ | — | >32 | 64 | 128 | 128 | 64 | 64 | 48 | 24 |
| VI | SALINE | 21 | − | ✓ | ✓ | ✓ | <4 | <4 | <4 | <4 | <4 | <4 | <4 | <4 |
| | | 22 | − | ✓ | ✓ | ✓ | <4 | <4 | <4 | <4 | <4 | <4 | <4 | <4 |
| | | 23 | + | ✓ | ✓ | ✓ | <4 | <4 | <4 | <4 | <4 | <4 | <4 | <4 |
| | | 24 | + | ✓ | ✓ | ✓ | <4 | <4 | <4 | <4 | <4 | <4 | <4 | <4 |

*Reciprocal of the dilution that caused a 50% plaque reduction
Pairs of animals were inoculated with (+) or without (−) incomplete Freund's adjuvant on the days indicated (✓)

TABLE 5

Immune status of vaccinated sheep after virulent virus challenge

| GROUP NO. | INOCULUM | SHEEP NO. | SERUM NEUTRALIZATION TITERS AGAINST BTV-10 (21 DAYS POST CHALLENGE) | CLINICAL REACTION INDEX | VIREMIA* (DAYS POST-CHALLENGE) |
|---|---|---|---|---|---|
| I | VP2: ~50 µg | 1 | 160 | 0.0 | — |
|   |   | 2 | 640 | 1.4 | 4–6 |
|   |   | 3 | 40 | 0.0 | — |
|   |   | 4 | 320 | 3.1 | — |
| II | VP2: ~100 µg | 5 | 40 | 0.0 | — |
|   |   | 6 | <20 | 0.0 | — |
|   |   | 7 | <20 | 0.0 | — |
|   |   | 8 | 80 | 0.0 | — |
| III | VP2: ~200 µg | 9 | 80 | 0.0 | — |
|   |   | 10 | 40 | 0.0 | — |
|   |   | 11 | 80 | 0.0 | — |
|   |   | 12 | <20 | 0.0 | — |
| IV | VP2: ~50 µg VP5: ~20 µg | 13 | 40 | 0.0 | — |
|   |   | 14 | 40 | 0.0 | — |
|   |   | 15 | 120 | 0.0 | — |
|   |   | 16 | 60 | 0.0 | — |
| V | VP1,VP5: (~20 µg, each) VP2; VP3: (~50 µg, each) VP6; VP7: (~100 µg, each) NS1;NS2: (~200 µg, each) NS3: (~20 µg) | 17 | 20 | 0.0 | — |
|   |   | 18 | 20 | 0.0 | — |
|   |   | 19 | <20 | 0.0 | — |
|   |   | 20 | 20 | 0.0 | — |
| VI | SALINE | 21 | >640 | 7.4 | 4–9 |
|   |   | 22 | 640 | 5.0 | 4–10 |
|   |   | 23 | 640 | 4.6 | 4–9 |
|   |   | 24 | >640 | 5.1 | 4–10 |

*Viremia assayed in eggs; + indicates none detected, numbers refer to days sheep blood tested positive for viremia.
Clinical Reaction Index: (a + b + c): (a) the fever score - the cumulative total of fever readings above 40° on days 3–14 after challenge (maximum score 12); (b) the lesion score - lesions of the mouth, nose and feet were each scored on a scale of 0–4 and added together (maximum score 12); (c) the death score - 4 points if death occurred within 14 days post-challenge.

Example 3

A preliminary study (#1) was also performed with Bluetongue CLPs (composed of VP3 and VP7) or VLPs (composed of VP3, VP7, VP2 and VP5). The effect of cholera toxin (CT) an an adjuvant was also examined on the immune responses to CLPs.

Groups of 2 BALB/c mice were immunized orally by intragastric intubation of immunogen in 0.5 ml bicarbonate buffer. Controls were administered PBS. Each group received 3 doses of CLPs or PBS 10 days apart. 200 μg CLP+10 μg CT for the first two doses, and 500 μg CLPs+10 μg CT for the third dose. A group of BALB/mice were immunized systematically with CLPs+Ribi adjuvant by intraperitoneal (i.p.) injection (2 mice given 10 μg and 2 given 40 μg).

In an expanded study (#2), groups of 5 BALB/c mice were immunized orally by intragastric (i.g.) intubation. Controls were administered i.g. PBS (n=5). Each group received 4 doses of CLP, CLP+CT, VLP+CT, or PBS 10 days apart, at a dose of 500 μg CLP or VLP and 10 μg cholera toxin (CT) per mouse. Serum and fecal pellets were collected at 7 days after each immunization.

Serum and fecal samples were assayed by ELISA for anti-BTV antibodies using gradient purified BTV-10 as antigen Serum was assayed for anti-BTV IgG and IgA, and fecal pellets were assayed for anti-BTV IgA.

Results

Oral administration of CLP+CT resulted in significant levels of serum IgG, serum IgA and mucosal IgA which increased sequentially as a function of immunization (see FIGS. 13–15). Results in studies #1 and #2 were comparable. After the fourth immunization with CLP+CT, >30,000 ng/ml serum IgG, 4,000 ng/ml serum IgA, and 1,400 ng mucosal IgA per 200 mg feces were generated. Serum IgG levels in orally immunized mice were roughly ⅕ the level of systematically immunized mice given less than 1/10th the dose of CLP.

Oral immunization with VLP+CT resulted in the development of serum IgG and IgA levels and mucosal IgA levels that were ½ to ⅔ the level of CLP+CT group. In the CLP without CT group, serum IgG levels were about ⅕ of the CLP+CT levels, but no serum or mucosal IgA was detected.

Because the booster doses increased IgG and IgA levels in both serum and feces, this study indicates that the mucosal IgA generated by oral immunization did not inhibit the immune response to repeated administration (i.e., did not produce immune exclusion).

Western blot analysis performed on the serum and fecal samples with the highest titers of antibody demonstrated that fecal and serum IgA preparations were unreactive. Serum IgG samples from orally immunized mice gave inconsistent reactivity with VP3 or VP7.

REFERENCES

1. Owen, R. L., Ermak, T. H. Structural specializations for antigen uptake and processing in the digestive tract. Springer Semin Immunopathol 12:139–153, 1990.
2. Neutra, M. R., Kraehenbuhl, J-P. Transepithelial transport and mucosal defence 1: the role of M cells. Trends in Cell Biol 2:134–138, 1992.
3. Kraehenbuhl, J-P., Neutra, M. R. Transepithelial transport and mucosal defence 11: secretion of IgA. Trends in Cell Biol 2:170–174, 1992.
4. Kiyono, H., McGhee, J. R., Mosteller, L. M. Eldridge, J. H., Koopman, W. J., Kearney, J. F., Michalek, S. M. J Exp Med 156:1115, 1982.

5. Kawanishi, H. Saltzman, L. E., Strober, W. Characteristics and regulatory function of murine ConA-induced, cloned T cells, obtained from Peyer's patches and spleen: mechanisms regulating isotype-specific immunoglobulin production by Peyer's patch B cells. J Immunol 129:475, 1982.

6. Kawanishi, H., Saltzman, L. E., Strober, W. Mechanisms regulating IgA-class specific immunoglobulin production in murine gut-associated lymphoid tissue. 1. T cells derived from Peyer' patches which switch sigM B cells to sigA B cells in vitro. J Exp Med 157:433, 1983.

7. Coffman, R. I., Shrader, B., Carty, J. Mossmann, T. R., Bond, M. W. A mouse T cell product that preferentially enhances IgA production. I. Biologic characterization. J. Immunol 139, 3685–90, 1987.

8. Bond, M. W., Shrader, B., Mossman, T. R., Coffman, R. L. A mouse T cells product that preferentially enhances IgA production 11. Physicochemical characterization. J Immunol 139:3691–3696, 1987.

9. Ermak, T. H., Owen, R. L. Differential distribution of lymphocytes and accessory cells in mouse Peyer's patches. Anat Record 215:144–152, 1986.

10. Bye, W. A., Allan, C. H., Trier, J. S. Structure, distribution and origin of M cells in Peyer's patches of mouse ileum. Gastroenterology 86:789–801, 1984.

11. Neutra, M. R., Phillips, T. L., Mayer, E. L., Fishkind, D. J. Transport of membrane-bound macromolecules by M cells in follicle-associated epithelium of rabbit Peyer's patch. Cell Tiss Res 247:537–546, 1987.

12. Wolf, J. L., Kauffman, R. S., Finberg, R., Dambrauskas, R., Fields, B. N., Trier, J. S. Determinants of reovirus interaction with the intestinal M cells and absorptive cells of murine intestine. Gastroenterology 85:291–300, 1983.

13. Owen, R. L., Pierce, N. F., Apple, R. T., Cray, W. C. Jr. M cell transport of *Vibrio cholerae* from the intestinal lumen into Peyer's patches; a mechanism for antigen sampling and for microbial transepithelial migration. J Infect Dis 153:1108–1118, 1986.

14. Marcial, M. S., Madara, J. L. Cryptosporodium: Cellular localization, structural analysis of absorptive cell-parasite membrane-membrane interactions in guinea pigs, and suggestions of protozoan transport of M cells. Gastroenterology 90:583–594, 1986.

15. Inman, L. R., Cantey, J. R. Specific adherence *Escherichia coli* (Strain RDEC-1) to membranous (M) cells of the Peyer's patch in *Escherichia coli* diarrhea in the rabbit. J Cain Invest 71:1–8, 1983.

16. Chiders, N. K., Benys, F. R., McGee, N. F., Michalek, S. M. Ultrastructural study of liposome uptake by M cells of rat Peyer's patch: an oral vaccine system for delivery of purified antigen. Regional Immunol 3:8–16, 1990.

17. Pappo, J., Ermak, T. H. Uptake and translocation of fluorescent latex particles by rabbit Peyer's patch follicle epithelium: a quantitative model for M cell uptake. Clin exp Immunol 76:144–148, 1989.

18. LeFevre, M. E., Warren, J. B., Joel, D. D. Particles and macrophages in murine Peyer's patches. Exp Cell Biol 53:121–129, 1985.

19. Eldridge, J. H., Staas, J. K., Meulbroek, J. A., McGhee, J. R., Tice, T. R., Gilley, R. M. Biodegradable microspheres as a vaccine delivery systems. Molecular Immunology 28:287–294, 1991.

20. Pappo, J. Ermak, T. H., Steger, H. J. Monoclonal antibody-directed targeting of fluorescent polystyrene microspheres to Peyer's patch M cells. Immunology 73, 1991.

21. Hewat, E. A., Booth, T. F., Roy, P. Structure of bluetongue virus particles by cryoelectron microscopy. J. Struct Biol 109:61–9, 1992.

22. Liu, H. M., Booth, T. F., Loudon, P. T., Roy, T. Interactions between bluetongue virus core and capsid proteins translated in vitro. J Gen Virol 73:2577–84, 1992.

23. Hewat, E. A., Booth, T. F., Loudon, P. T., Roy, T. Three-dimensional reconstruction of baculovirus expressed bluetongue virus core-like particles by cryoelectron microscopy. Virology 189:10–20, 1992.

24. Prasad, B. V., Yamaguchi, S., Roy, P. Three-dimensional structure of single-shelled bluetongue virus. J Virol 66:135–42, 1992.

25. French, T. J., Marshall, J. J., Roy, P. Assembly of double-shelled, virus-like particles of bluetongue virus by the simultaneous expression of four structural proteins. J Virol 64:5695–700, 1990.

26. French, T. J., Roy, P. Synthesis of bluetongue virus (BTV) corelike particles by a recombinant baculovirus expressing the two major structural core proteins of BTV. J Virol 64:1530–6, 1990.

27. Roy, P., French, T., Erasmus, B. J. Protective efficacy of virus-like particles for bluetongue disease. Vaccine 10:28–32, 1992.

28. Roy, P., Urakawa T., Van Dijk, A. A., Erasmus, B. J. Recombinant virus vaccine for bluetongue disease in sheep. J Virol 64:1998–2003, 1990.

29. Roy, P. From genes to complex structures of bluetongue virus and their efficacy as vaccines. Vet Microbiol 33:155–68, 1992.

30. Belyaev, A. S.; Roy, P. Presentation of hepatitis B virus pre S2 epitope on bluetongue virus core-like particles. Virology 190:840–4, 1992.

31. Elson, C.O., Ealding, W. Generalized systemic and mucosal immunity in mice after mucosal stimulation with cholera toxin. J. Immunol 132, 2636–2741, 1984.

---

We claim:

1. A method of inducing a mucosal and a systemic immune response in a host, said method comprising the step of orally administering to a mucosal surface of said host a bluetongue antigen in the form of virus core like particles or in the form of virus like particles and in an amount effective to induce said immune response.

2. A method according to claim 1, wherein said antigen is administered with an adjuvant.

3. A method according to claim 2, wherein said adjuvant is cholera toxin.

4. A method according to claim 1, wherein said virus core like particles comprise VP3 and VP7.

5. A method according to claim 1, wherein said virus like particles comprise VP3, VP7, VP2 and VP5.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:1:

GTAATAAAAA AACCTATAAA TACGGATCCG GTTATT        36

( 2 ) INFORMATION FOR SEQ ID NO:2:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:2:

GTAATAAAAA AACCTATAAA TACGGATCCG GTTAAAAGT GTTCTCCTAC TCGCAGAAGA        60

TGGGGAA        67

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:3:

ACGAAATGCT TGAACGCGGA TCCGGTTATT        30

( 2 ) INFORMATION FOR SEQ ID NO:4:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:4:

GTAATAAAAA AACCTATAAA TACGGATCGG GGTTAAAAGA GTGTTCTACC ATGGAGAA        58